(12) United States Patent
Barkai et al.

(10) Patent No.: US 9,682,067 B2
(45) Date of Patent: Jun. 20, 2017

(54) METHODS OF IMPROVING COGNITIVE FUNCTION

(71) Applicant: Carmel-Haifa University Economic Corp., Haifa (IL)

(72) Inventors: Edi Barkai, Haifa (IL); Dietmar Schmitz, Berlin (DE)

(73) Assignee: Carmel-Haifa University Economic Corp., Haifa (IL)

( * ) Notice: Subject to any disclaimer, the term of this patent is extended or adjusted under 35 U.S.C. 154(b) by 722 days.

(21) Appl. No.: 13/928,008

(22) Filed: Jun. 26, 2013

(65) Prior Publication Data

US 2014/0011850 A1  Jan. 9, 2014

Related U.S. Application Data

(63) Continuation of application No. PCT/IL2011/050074, filed on Dec. 25, 2011.

(60) Provisional application No. 61/427,186, filed on Dec. 26, 2010.

(51) Int. Cl.
| | | |
|---|---|---|
| A61K 31/40 | (2006.01) | |
| A61K 31/42 | (2006.01) | |
| A61K 31/401 | (2006.01) | |
| A61K 31/404 | (2006.01) | |
| A61K 31/198 | (2006.01) | |
| A61K 31/513 | (2006.01) | |

(52) U.S. Cl.
CPC ............ *A61K 31/42* (2013.01); *A61K 31/198* (2013.01); *A61K 31/40* (2013.01); *A61K 31/401* (2013.01); *A61K 31/404* (2013.01); *A61K 31/513* (2013.01)

(58) Field of Classification Search
None
See application file for complete search history.

(56) References Cited

U.S. PATENT DOCUMENTS 5,731,348 A    3/1998  Gu
2006/0191028 A1  8/2006  Doucette et al.

FOREIGN PATENT DOCUMENTS

| DE | 19513630 A1 | 10/1996 |
|---|---|---|
| EP | 0374257 A1 | 6/1990 |
| EP | 0600741 A1 | 6/1994 |
| GB | 2316616 A | 3/1998 |

OTHER PUBLICATIONS

Brosh et al., (2006) Learning-induced reversal of noradrenalin's effect on neuronal excitability. J Neurophysiol 96 (4):1728-1733.
Cohen-Matsliah et al., (2007) A novel role for Extracellular Signal-Regulated Kinase in maintaining long-term memory-relevant excitability changes. J Neurosci 27(46):12584-12589.
Disterhoft and Oh (2006) Learning, aging and intrinsic neuronal plasticity. Trends Neurosci 29(10):587-599.
Donevan et al., (1998) The methylglutamate, SYM 2081, is a potent and highly selective agonist at kainate receptors. J Pharmacol Exp Ther 285(2): 539-545.
Fisahn et al., (2005) The Kainate receptor subunit GluR6 mediates metabotropic regulation of the slow and medium AHP currents in mouse hippocampal neurons. J Physiol 562(1):199-203.
Grabauskas et al., (2007) Protein kinase signalling requirements for metabotropic action of kainate receptors in rat CA1 pyramidal neurones. J Physiol 579(2):363-373.
Melyan et al., (2002) Metabotropic-mediated kainate receptor regulation of IsAHP and excitability in pyramidal cells. Neuron 34(1):107-114.
Melyan et al., (2004) Metabotropic regulation of intrinsic excitability bysynaptic activation of kainate receptors. J Neurosci 24(19):4530-4534.
Moyer et al., (1996) Trace eyeblink conditioning increases CA1 excitability in a transient and learning specific manner. J Neurosci 16(17):5536-5546.
Oh et al., (2003) Watermaze learning enhances excitability of CA1 pyramidal neurons. J Neurophysiol 90 (4):2171-2179.
Power et al., (2002) Age-related enhancement of the slow outward calcium-activated potassium current in hippocampal CA1 pyramidal neurons in vitro. J Neurosci 22(16):7234-7243.
Saar and Barkai (2003) Long-term modifications in intrinsic neuronal properties and rule learning in rats. Eur J Neurosci 17(12):2727-2734.
Saar and Barkai (2009) Long-Lasting Maintenance of Learning-Induced Enhanced Neuronal Excitability: Mechanisms and Functional Significance. Mol Neurobiol 39(3):171-177.
Saar et al., (1998) Reduced after-hyperpolarization in rat piriform cortex pyramidal neurons is associated with increased learning capability during operant conditioning. Eur J Neurosci 10(4)1518-1523.
Saar et al., (2001) Long lasting Cholinergic modulation underlies rule learning in rats. J Neurosci 21(4):1385-1392.
Thompson et al., (1996) Transient changes in excitability of Rabbit CA3 neurons with a time course appropriate to support memory consolidation. J Neurophysiol 76(3):1836-1849.
Zelcer et al., (2006) A cellular correlate of Learning-induced metaplasticity in the hippocampus. Cereb Cortex 16 (4):460-468.
Ahmadian et al., (1997) (S)-homo-AMPA, a specific agonist at the mGlu6 subtype of metabotropic glutamic acid receptors. J Med Chem 40(22): 3700-5.
Clarke et al., (1997) A hippocampal GluR5 kainate receptor regulating inhibitory synaptic transmission. Nature 389 (6651): 599-603.
Hampson and Manalo (1998) The activation of glutamate receptors by kainic acid and domoic acid. Nat Toxins 6(3-4): 153-8.

*Primary Examiner* — Shobha Kantamneni
(74) *Attorney, Agent, or Firm* — Vorys, Sater, Seymour & Pease LLP

(57) ABSTRACT

A method of improving cognitive function or treating cognitive dysfunction is provided. The method is based on activating a kainate receptor or a glutamate GluR6 receptor by kainate or a glutamate GluR6 receptor activator such as an agonist. Additionally, a method of enhancing a learning ability by activating a kainate receptor such as the glutamate GluR6 receptor via kainate or a glutamate GluR6 receptor activator such as an agonist is provided.

11 Claims, 9 Drawing Sheets

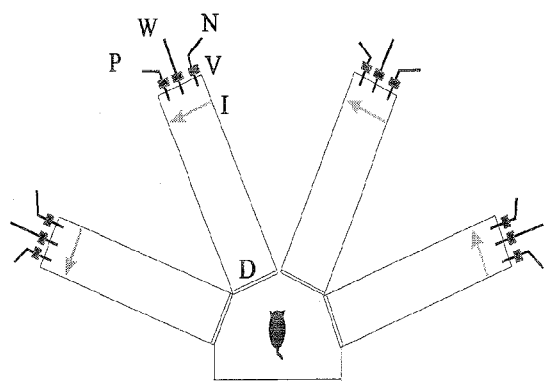
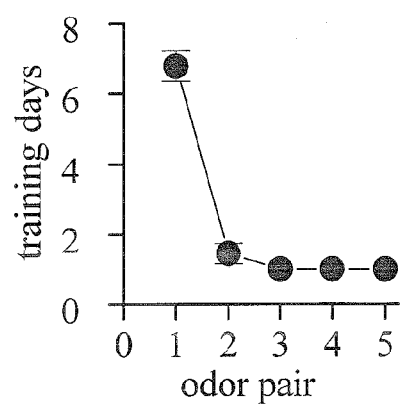
FIGURE 1A
FIGURE 1B
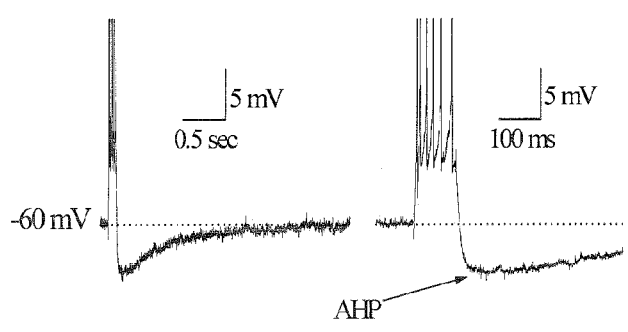
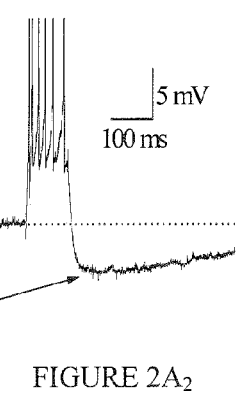
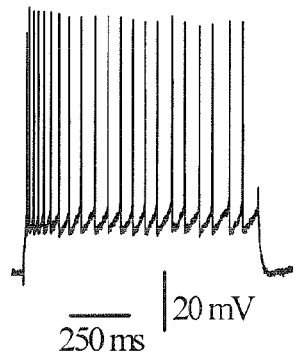
FIGURE 2A$_1$     FIGURE 2A$_2$     FIGURE 2B

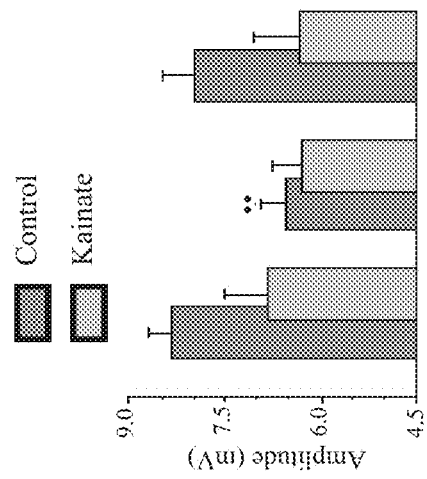
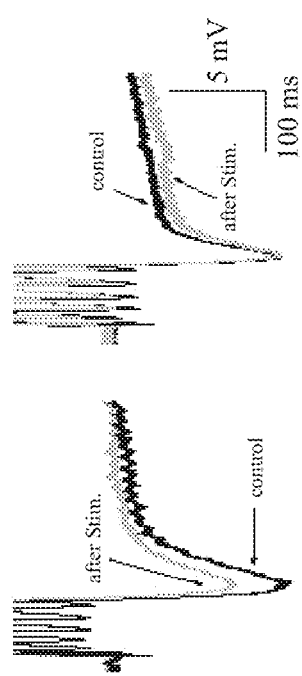
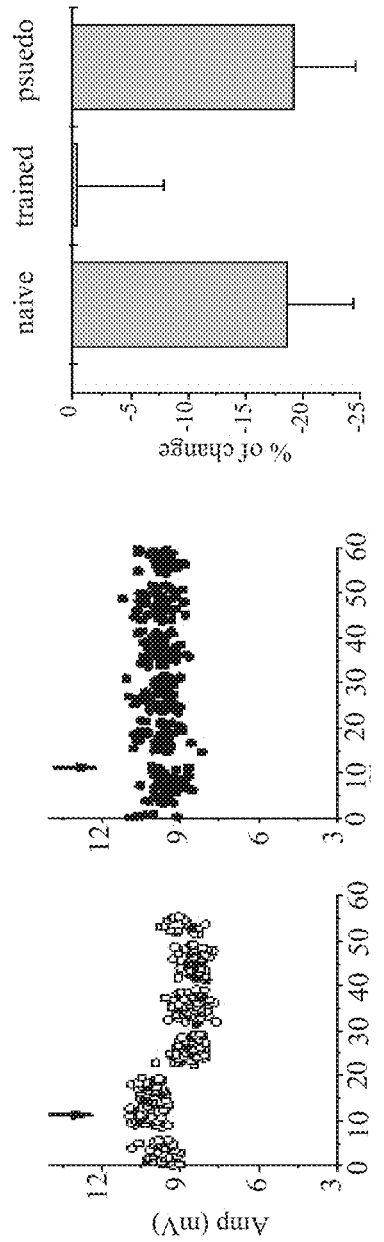
FIGURE 7A₁
FIGURE 7A₂
FIGURE 7B₁
FIGURE 7B₂
FIGURE 7C₁
FIGURE 7C₂

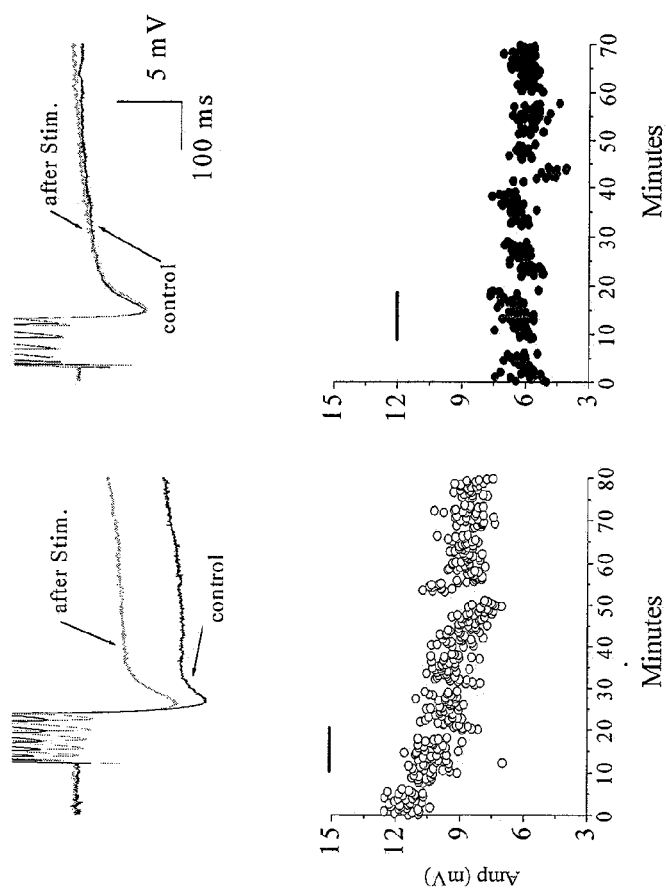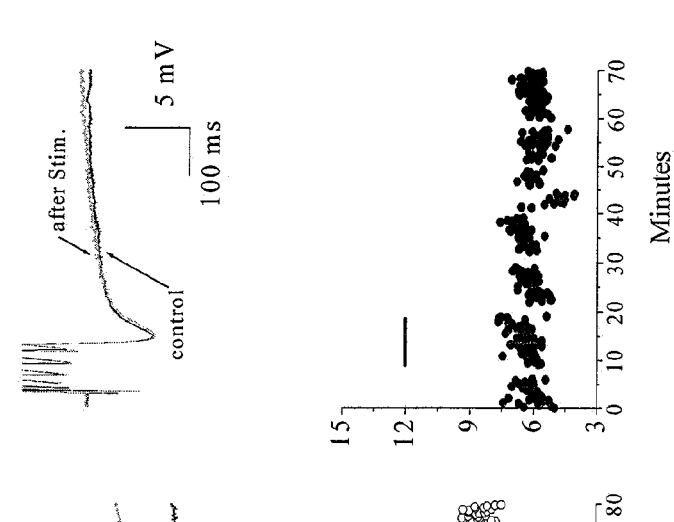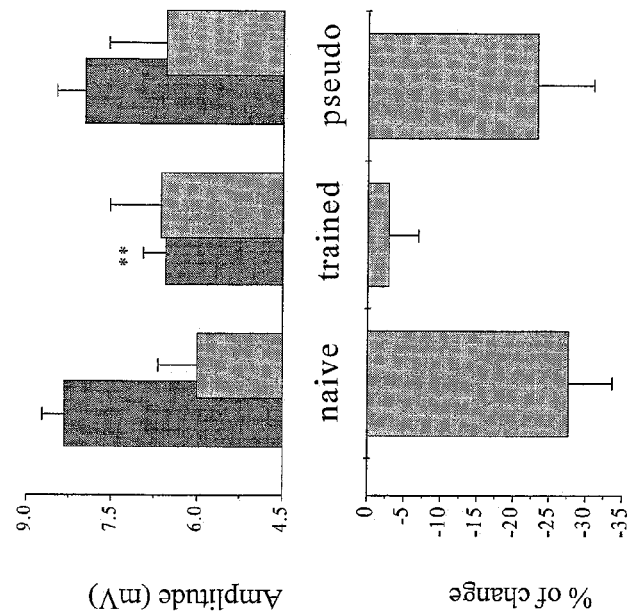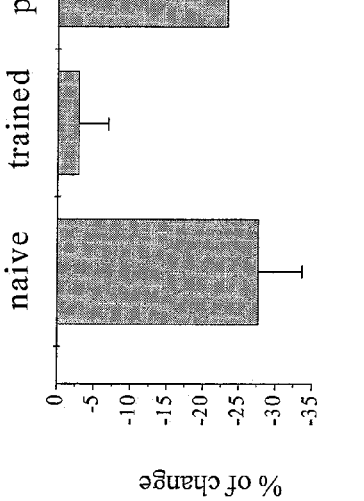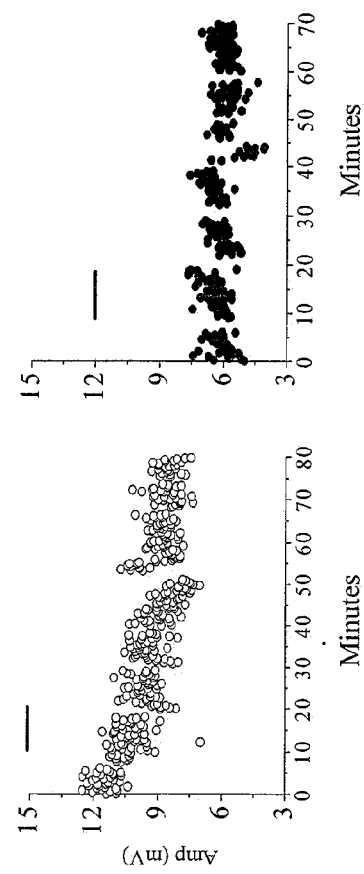

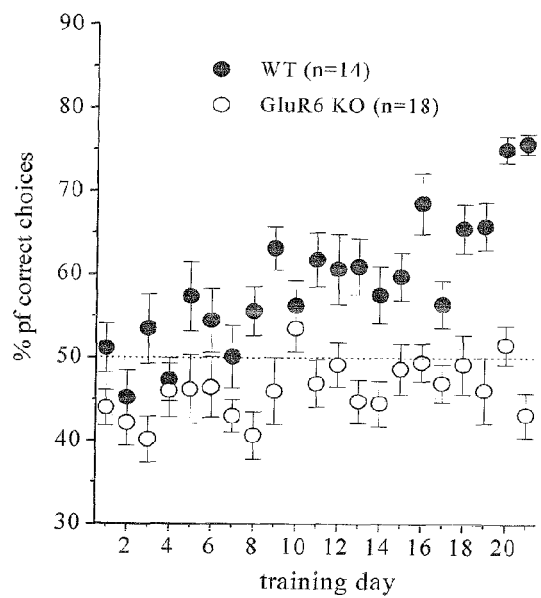
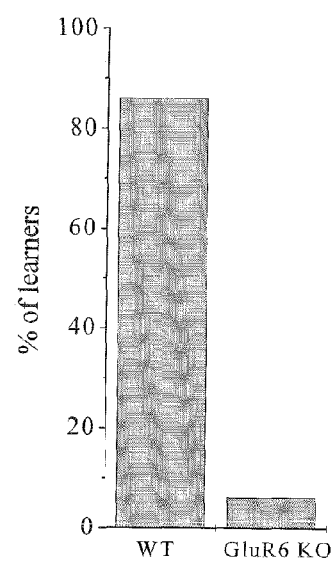
FIGURE 9A
FIGURE 9B

METHODS OF IMPROVING COGNITIVE FUNCTION

FIELD OF INVENTION

A method for improving cognitive function of a subject such as enhancing a learning ability of a subject in need thereof by contacting a glutamate GluR6 receptor in the subject with a glutamate GluR6 receptor activator is disclosed.

BACKGROUND OF THE INVENTION

Cognition can be described as a mental process that includes the ability to memory, attention, learning, perception, action, problem solving and mental imagery.

Cognitive dysfunctions are characterized clinically by progressive loss of memory, cognition, reasoning, judgment and emotional stability that gradually leads to profound mental deterioration and ultimately death. Among these diseases, Alzheimer's disease is considered as the most common and is believed to represent the fourth most common medical cause of death in the United States.

Cognitive ability may decline as a normal consequence of aging. A significant population of elderly adults experiences a decline in cognitive ability that exceeds what is typical in normal aging. Such age-related loss of cognitive function is characterized clinically by progressive loss of memory, cognition, reasoning, and judgment. Mild Cognitive Impairment (MCI), Age-Associated Memory Impairment (AAMI), Age-Related Cognitive Decline (ARCD) or similar clinical groupings are among those related to such age-related loss of cognitive function.

Learning is acquiring new knowledge, behaviors, skills, values, or preferences and involves synthesizing different types of information. The ability to learn is possessed by humans, animals and some machines. Progress over time tends to follow learning curves.

A method of inducing a learning ability is desirable and can provide an important advantage in term of reaching superior brainpower, mental capacity, the ability to comprehend and/or to understand and profit from experience.

Human learning occurs as part of education, personal development, or training. It may be goal-oriented and may be aided by motivation. The study of how learning occurs is part of neurobiology, neuropsychology, educational psychology, learning theory, and pedagogy.

Learning can occur as a result of habituation, classical conditioning, operant conditioning and higher order forms learning, such as rule learning (defined as the ability to extract generalizable rules from specific experiences) and learning set (defined as a readiness or predisposition to learn developed from previous learning experiences, as when an organism learns to solve each successive problem of equal or increasing difficulty in fewer trials, seen in many animal species, or as a result of more complex activities such as play. Learning is not exclusively dependent on conscious awareness.

Learning is the process by which new information is acquired; memory is the process by which that knowledge is retained. Memory can be divided into two types: 1) Explicit memory is the conscious acquisition of knowledge about people, places and things. It occurs in the highly developed vertebrate brain, mainly in the diencephalic structure. 2) Implicit memory is the non conscious learning of motor skills and other tasks. It does not depend on the temporal lobe, but involves the sensory, motor associated pathways in the expression of the learning process. This type of memory can be studied in higher invertebrates whereas explicit learning is only studied in mammals.

Two areas of great interest are: the actual mechanism of learning and the process of consolidation which relates to how something that is learned is then stored as memory. The mechanisms underlying learning in the mammalian brain have been first elucidated by the concept of long term potentiation and in later by describing single cell modifications that accompany learning.

The actual mechanism of learning includes modulation of synaptic strength. Most of the effort made thus far to explore the cellular bases of learning and memory is in the frame of studying the long term potentiation (LTP) phenomenon. LTP is an artificial experimental model, in which long lasting increase in synaptic effectiveness is induced high frequency of stimulation of afferent fibers. Although long term potentiation occurs throughout the nervous system, its focus has mainly been in the hippocampus which is involved in the formation of certain memories. Characteristics of long term potentiation are associated with memory storage. Thus far, it has been shown that artificial induction of long term potentiation has no clear effect on learning.

Memory storage seems to be influenced by the strength and structure of synaptic connections. Long term memory, lasts for days, weeks and is associated with the growth of new synaptic connections activated by altered gene expression and de-novo protein synthesis.

There is an unmeet need for methods and compositions for improving cognitive function of a subject, including but not limited to, enhancing the learning and memory ability of a subject.

SUMMARY OF THE INVENTION

In one embodiment, the present invention provides a method of improving a cognitive function of a subject, comprising the step of administering to the subject a composition comprising an effective amount of a glutamate GluR6 receptor activator or a kainate receptor activator, thereby improving the cognitive function of said subject. In particular embodiments of the methods of the invention, said improving the cognitive function is enhancing the learning ability of said subject.

In another embodiment, the present invention provides a kainate receptor activator for use in improving the cognitive function of a subject. In yet another embodiment, the present invention provides a kainite receptor activator for the preparation of a medicament for improving the cognitive function of a subject.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIGS. 1A-B are directed to olfactory discrimination training-apparatus and rule learning. FIG. 1A is a schematic description of the 4-arm maze. FIG. 1B is a graph showing the odor pair training progression.

FIGS. 2A-2B are directed to post-burst after-hyperpolarization (AHP) and neuronal adaptation in CA1 pyramidal neurons. FIGS. 2A1 and 2A2 are graphs depicting recordings for AHP measurements.

FIG. 3A is a bar graph depicting AHP reduction (relative to control) in neurons of 'mildly trained' rats. FIG. 3B is a bar graph showing that training suspension affects learning capability (measured as percentage of success).

FIG. 4A depicts a bar graph showing the relative amplitude of AHP in hippocampal neurons (normalized to averaged values of pseudo trained). FIG. 4B depicts a graph showing the cumulative frequency histograms for AHP amplitude in neurons from trained, pseudo trained and naive rats.

FIG. 5A depicts graphs showing the repetitive action potentials' firing in neurons from a pseudo trained (top panel) and a trained (lower panel) rats in response to 1 sec pulse with stimulus intensity of $I_{th}x2$. FIG. 5B depicts a graph showing spike firing adaptation in pyramidal neurons.

FIG. 6A depicts a graph showing that olfactory discrimination (OD) learning in the olfactory maze enhances subsequent learning in the Morris water maze. FIG. 6B depicts a graph showing that OD trained rats lose their advantage over control rats in water maze learning when the post-burst AHP resumes its control value.

FIGS. 7A-C are directed to learning occludes stimulation-induced AHP reduction. FIG. 7A1 is a graph showing a trace recorded from pseudo trained neurons, before and 50 min after application of repetitive stimulation. FIG. 7A2 is a graph showing the amplitude of the AHP measured continuously, prior to, and after stimulus. FIG. 7B1 and FIG. 7B2 show a trace from a trained neurons, before and 50 min after applying repetitive stimulation. Arrows note time of repetitive synaptic stimulation. The bar graphs of FIG. 7C1 and FIG. 7C2 show the differences in AHP amplitudes between neurons from trained and control groups are abolished after repetitive synaptic activation. Values represent mean+SEM.

FIGS. 8A-C are directed to learning occludes kainate-induced reduction in the post-burst AHP. FIG. 8A1 is a graph showing a trace of pseudo trained neurons, before and 50 minutes after a 10 min application of kainate. FIG. 8A2 is a graph showing the amplitude of the post burst AHP measured continuously prior to and after stimulus. Here too, AHP reduction is coupled with a delay of several minutes after termination of kainate application (line). FIG. 8B1 is a graph showing a trace for trained neurons, before and 50 minutes after application of kainate. FIG. 8B2 is a graph showing continuous measurements of the responses show that the post burst AHP was not affected by kainate. FIG. 8C1 and FIG. 8C2 are bar graphs that show the differences in AHP amplitudes between neurons from trained and control groups is abolished after kainate application. Following repetitive synaptic activation the averaged values of the post burst AHP are similar in all groups.

FIGS. 9A-B are directed to learning requires active and inducible GluR6. FIG. 9A is a graph showing that twelve of the 14 Wild Type (WT) mice completed the task; however, in sharp contrast GluR6 knockout mice do not show any improvement by training progression. FIG. 9B is a bar graph showing that most WT mice reach the criterion for rule learning while GluR6 knockout rats exhibit clear learning deficiency.

FIG. 10A is a graph showing in response to a 1 sec depolarizing pulse with stimulus intensity of $I_{th}x2$, kainite application enhanced repetitive spike firing in neurons of WT mice. FIG. 10B is a bar graph depicting the number of spikes following kainate application in GluR6+/+ and GluR6−/− neurons, as opposed to control, (n) depicts the number of neurons.

DETAILED DESCRIPTION OF THE INVENTION

Figure 3A:
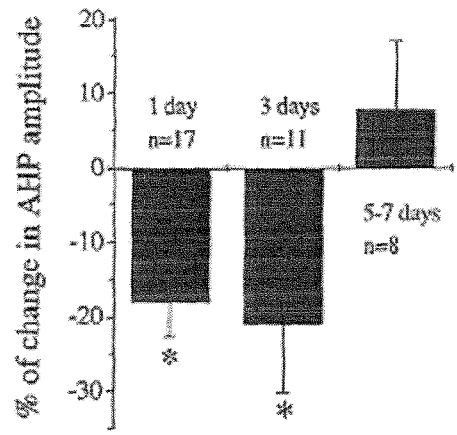
FIGS. 3A-3B are directed to after-hyperpolarization (AHP) reduction and the impact on learning ability/capability.

The present invention provides compositions and methods for improving the cognitive function of a subject, including but not limited to enhancing the learning and/or the memory ability of said subject. In some embodiments, the present invention provides methods for treating a cognitive dysfunction in a subject, including but not limited to dementia.

The present invention is based, in part, on the finding that kainate receptor activation mediates long-lasting reductions of after-hyperpolarization (AHP) and consequently enhancement in neuronal excitability. As exemplified herein below, activating the kainate receptor by kainite application enhanced the biophysical repetitive spike firing in neurons of wild type mice as apposed GluR6 knockout mice. Remarkably, kainite receptor activation reduced the averaged time required for complex olfactory learning.

In one embodiment, the present invention provides a method for enhancing a learning ability of a subject, comprising the step of administering to the subject a composition comprising an effective amount of a kainate receptor activator such as the glutamate GluR6 receptor activator. In another embodiment, the kainate receptor activator is the glutamate GluR6 receptor activator. In another embodiment, GluR6 is also known as GRIK2.

In another embodiment, the present invention provides a method for the improvement of cognitive function or treatment of a cognitive dysfunction by administering to a subject in need of improvement of cognitive function or treatment of a cognitive dysfunction a therapeutically-effective amount of a kainate receptor activator such as the glutamate GluR6 receptor activator. In another embodiment, the cognitive function is memory. In another embodiment, the cognitive function is learning. In another embodiment, the cognitive dysfunction is dementia. In another embodiment, the cognitive dysfunction is Alzheimer's disease. In another embodiment, the cognitive dysfunction is memory impairment. In another embodiment, the cognitive dysfunction is age associated memory impairment. In another embodiment, the cognitive dysfunction is a learning deficit.

Kainate receptors, as opposed to other ionotropic glutamate receptors, e.g., AMPA and NMDA, are metabotropic receptors. Without wishing to be bound to any mechanism or theory of action, the invention is based, in part, on the findings that activation of the kainite receptor such as the glutamate GluR6 receptor enhances neuronal excitability by affecting their intrinsic membranal properties, thereby setting a time window for enabling activity-dependent synaptic modifications. Wide spread modifications in neuronal excitability increases the amount of information (expressed in averaged action potential firing rate) processed in the network composed of these neuron. As demonstrated hereinbelow, enhanced intrinsic neuronal excitability results with enhanced cognitive function (e.g., learning).

The Glutamate GluR6 Receptor Activator

In another embodiment, induction of a kainate receptor such as the glutamate GluR6 receptor results in enhancement of a learning ability/capability and/or cognitive function. In another embodiment, induction of a kainate receptor such as the glutamate GluR6 receptor is a specific induction of a glutamate GluR6 receptor but not other glutamate receptors. In another embodiment, the affinity of a glutamate GluR6 receptor activator of the invention is at least 5 fold greater to a glutamate GluR6 receptor than to any other glutamate receptor. In another embodiment, the affinity of a glutamate GluR6 receptor activator of the invention is at least 10 fold greater to a glutamate GluR6 receptor than to any other glutamate receptor. In another embodiment, the affinity of a glutamate GluR6 receptor activator of the invention is at least 50 fold greater to a glutamate GluR6 receptor than to any other glutamate receptor. In another embodiment, the affinity of a glutamate GluR6 receptor activator of the invention is at least 100 fold greater to a glutamate GluR6 receptor than to any other glutamate receptor.

In another embodiment, the kainate receptor activator such as the glutamate GluR6 receptor (GLuR6 receptor) activator of the invention is a kainate receptor agonist and/or GLuR6 receptor agonist. In another embodiment, the kainate receptor activator such as a GLuR6 receptor activator of the invention is a kainate receptor stimulator or GLuR6 receptor stimulator. In another embodiment, the kainate receptor activator or GLuR6 receptor activator of the invention is a kainate receptor ligand or GLuR6 receptor ligand. In another embodiment, the kainate receptor activator or GLuR6 receptor activator is a peptide or a protein. In another embodiment, the kainate receptor activator or GLuR6 receptor activator is a small molecule. In another embodiment, the kainate receptor activator or GLuR6 receptor activator is an organic molecule.

In another embodiment, the kainate receptor activator or GLuR6 receptor activator is kainate. In another embodiment, the kainate receptor activator or GLuR6 receptor activator is kainic acid. In another embodiment, the kainate receptor activator or GLuR6 receptor activator is (2S,3S,4S)-3-(Carboxymethyl)-4-prop-1-en-2-ylpyrrolidine-2-carboxylic acid. In another embodiment, the kainite receptor activator or GLuR6 receptor activator is (RS)-2-amino-4-(3-hydroxy-5-methylisoxazol-4-yl)butyric acid. In another embodiment, the kainate receptor activator or GLuR6 receptor activator is (2S,3S,4S)-Carboxy-4-(1-methylethenyl)-3-pyrrolidineacetic acid 4-methoxy-7-nitro-1H-indolinyl amide. In another embodiment, the kainate receptor activator or GLuR6 receptor activator is domoic acid. In another embodiment, the kainate receptor activator or GLuR6 receptor activator is (RS)-2-Amino-3-(3-hydroxy-5-tert-butyl-isoxazol-4-yl) propanoic acid. In another embodiment, the kainate receptor activator or GLuR6 receptor activator is (S)-(−)-5-Iodowillardiine, (2S,4R)-4-Methylglutamic acid. In another embodiment, the kainate receptor activator or GLuR6 receptor activator is a combination of kainate and/or GLuR6 receptor activators. In another embodiment, the kainite receptor activator or GLuR6 receptor activator is (RS)-2-amino-4-(3-hydroxy-5-methylisoxazol-4-yl)butyric acid.

In another embodiment, GLuR6 receptor activator of the invention is a specific agonist for the GLuR6 receptor. In another embodiment, the GLuR6 receptor activator is at least 5 fold more selective for GLuR6 receptor over other glutamate receptors and/or AMPA and NMDA receptors. In another embodiment, the GLuR6 receptor activator is at least 10 fold more selective for GLuR6 receptor over other glutamate receptors and/or AMPA and NMDA receptors. In another embodiment, the GLuR6 receptor activator is at least 20 fold more selective for GLuR6 receptor over other glutamate receptors and/or AMPA and NMDA receptors. In another embodiment, the GLuR6 receptor activator is at least 50 fold more selective for GLuR6 receptor over other glutamate receptors and/or AMPA and NMDA receptors. In another embodiment, the GLuR6 receptor activator is at least 100 fold more selective for GLuR6 receptor over other glutamate receptors and/or AMPA and NMDA receptors. In another embodiment, the GLuR6 receptor activator is at least 200 fold more selective for GLuR6 receptor over other glutamate receptors and/or AMPA and NMDA receptors. In another embodiment, the GLuR6 receptor activator is at least 1000 fold more selective for GLuR6 receptor over other glutamate receptors and/or AMPA and NMDA receptors.

Cognitive Function

In the method of the invention, the improving cognitive function can be achieved in healthy subjects as like as in subjects suffering from cognitive dysfunctions. In another embodiment, improving cognitive function includes promoting cognitive function and/or preserving cognitive function in a subject.

The term "cognitive function" as used herein, refers to any higher order intellectual brain process or brain state, respectively, involved in learning and/or memory including, but not limited to, attention, information acquisition, information processing, working memory, short-term memory, long-term memory, anterograde memory, retrograde memory, memory retrieval, discrimination learning, decision-making, inhibitory response control, attentional set-shifting, delayed reinforcement learning, reversal learning, the temporal integration of voluntary behavior, and expressing an interest in one's surroundings and self-care.

In humans, cognitive function may be measured by means known in the art, for example and without limitation, by the clinical global impression of change scale (CIBIC-plus scale); the Mini Mental State Exam (MMSE); the Neuropsychiatric Inventory (NPI); the Clinical Dementia Rating Scale (CDR); the Cambridge Neuropsychological Test Automated Battery (CANTAB); the Sandoz Clinical Assessment-Geriatric (SCAG), the Buschke Selective Reminding Test (Buschke and Fuld, 1974); the Verbal Paired Associates subtest; the Logical Memory subtest; the Visual Reproduction subtest of the Wechsler Memory Scale-Revised (WMS-R) (Wechsler, 1997); the Benton Visual Retention Test, or the explicit 3-alternative forced choice task. See Folstein et al, J Psychiatric Res 12: 189-98, (1975); Robbins et al, Dementia 5: 266-81, (1994); Rey, L'examen clinique en psychologie, (1964); Kluger et al, J Geriatr Psychiatry Neurol 12:168-79, (1999); Marquis et al, 2002 and Masur et al, 1994.

In animal model systems, cognitive function may be measured in various conventional ways known in the art, including using a Morris Water Maze (MWM) (as exemplified herein-below), Barnes circular maze, elevated radial arm maze, T maze or any other mazes in which the animals use spatial information. Other tests known in the art may also be used to assess cognitive function, such as novel object recognition and odor recognition tasks (as exemplified herein-below).

Cognitive function may also be measured using imaging techniques such as Positron Emission Tomography (PET), functional magnetic resonance imaging (fMRI), Single Photon Emission Computed Tomography (SPECT), or any other imaging technique that allows one to measure brain function. In animals, cognitive function may also be measured with electrophysiological techniques.

In another embodiment, the invention provides methods for preserving cognitive function. In some embodiments, preserving cognitive function is affecting normal or impaired cognitive function such that it does not decline or does not fall below that observed in the subject upon first presentation or diagnosis, or delays such decline.

Typically, treating a disorder of cognitive function according to the present invention includes treating, controlling, preventing and/or reducing one or more clinical signs (i.e., symptoms) of cognitive impairment in a subject in need thereof. These impairments can result from disorders such as age-associated memory dysfunction, memory loss, mild cognitive impairment, cognitive dysfunction syndrome, and dementias. Such dementias include, but are not limited to, Alzheimer's disease, Lewy body dementia, vascular dementia, dementia caused by chronic cerebral ischemia, AIDS dementia, dementia caused by Parkinson's disease, dementia caused by amyotrophic lateral sclerosis, dementia caused by brain trauma, dementia caused by Huntigton's disease, dementia caused by multiple sclerosis, dementia caused by Pick's disease, dementia caused by vascular disease, dementia caused by organ system failure, dementia caused by metabolic diseases, and dementia caused by infectious. Generally recognized compendiums of disorders that accompanied with decline of cognitive functions are Merck Manual of Diagnosis and Therapy. Sect. 14 Neurologic Disorders, Chapt. 171. Merck Manual of Geriatrics Sect. 5, Chapt. 40.

In some embodiments, promoting cognitive function is affecting impaired cognitive function so that it more closely resembles the function of a normal, unimpaired subject. Cognitive function may be promoted to any detectable degree, but in humans preferably is promoted sufficiently to allow an impaired subject to carry out daily activities of normal life at the same level of proficiency as a normal, unimpaired subject.

As used herein, the term "impaired cognitive function", "cognitive impairment" or "cognitive dysfunction" as used herein refers to cognitive function in subjects that is not as robust as that expected in a normal, unimpaired subject. In some cases, cognitive function is reduced by about 5%, about 10%, about 30%, or more, compared to cognitive function expected in a normal, unimpaired subject. In some cases, "cognitive impairment" or "cognitive dysfunction" in subjects affected by aged-related cognitive impairment refers to cognitive function in subjects that is not as robust as that expected in an aged-matched normal, unimpaired subject, or the function of a young adult subject (i.e. subjects with mean scores for a given age in a cognitive test).

In another embodiment, the present invention provides methods for promoting or enhancing cognitive function in a subject affected by age-related cognitive. Typically, promoting cognitive function in a subject affected by age-related cognitive refers to affecting impaired cognitive function so that it more closely resembles the function of an aged-matched normal, unimpaired subject, or the function of a young adult subject. Cognitive function of that subject may be promoted to any detectable degree, but in humans preferably is promoted sufficiently to allow an impaired subject to carry out daily activities of normal life at the same level of proficiency as an aged-matched normal, unimpaired subject or as a young adult subject.

"Age-related cognitive impairment" refers to cognitive impairment in aged subjects, wherein their cognitive function is not as robust as that expected in an age-matched normal subject or as that expected in young adult subjects. In some cases, cognitive function is reduced by about 5%, about 10%, about 30%, or more, compared to cognitive function expected in an age-matched normal subject. In some cases, cognitive function is as expected in an age-matched normal subject, but reduced by about 5%, about 10%, about 30%, about 50% or more, compared to cognitive function expected in a young adult subject. Age-related impaired cognitive function may be associated with Mild Cognitive Impairment (MCI) (including amestic MCI and non-amnestic MCI), Age-Associated Memory Impairment (AAMI), and Age-related Cognitive Decline (ARCD).

"Mild Cognitive Impairment" or "MCI" refers to a condition characterized by isolated memory impairment unaccompanied other cognitive abnormalities and relatively normal functional abilities. One set of criteria for a clinical characterization of MCI specifies the following characteristics: (1) memory complaint (as reported by patient, informant, or physician), (2) normal activities of daily living (ADLs), (3) normal global cognitive function, (4) abnormal memory for age (defined as scoring more than 1.5 standard deviations below the mean for a given age), and (5) absence of indicators of dementia (as defined by DSM-IV guidelines).

"Age-Associate Memory Impairment (AAMI)" refers to a decline in memory due to aging. A patient may be considered to have AAMI if he or she is at least 50 years old and meets all of the following criteria: a) The patient has noticed a decline in memory performance, b) The patient performs worse on a standard test of memory compared to young adults, c) All other obvious causes of memory decline, except normal aging, have been ruled out (in other words, the memory decline cannot be attributed to other causes such as a recent heart attack or head injury, depression, adverse reactions to medication, Alzheimer's disease, etc.).

"Age-Related Cognitive Decline (ARCD)" refers to declines in memory and cognitive abilities that are a normal consequence of aging in humans.

Alzheimer's disease (AD) is characterized by memory deficits in its early phase. Later symptoms include impaired judgment, disorientation, confusion, behavior changes, trouble speaking, and motor deficits. Histologically, AD is characterized by beta-amyloid plaques and tangles of protein tau.

Enhancing Learning

In another embodiment, the term enhancing is interchangeable with the terms "promoting", "intensifying", "improving", "increasing", "inducing", and "expanding". In another embodiment, the term enhancing is used for restoring learning capability after a decline in a learning capability.

In another embodiment, the term learning according to the invention includes memory. In another embodiment, the term learning according to the invention includes consolidation which relates to how something that is learned is then stored as memory. In another embodiment, the term learning according to the invention includes memory storage. In another embodiment, enhancing learning is enhancing a training capability and/or capacity. In another embodiment, the term learning comprises a process that will modify a subsequent behavior and/or the ability to remember past experiences. In another embodiment, the term learning comprises the ability to study. Therefore, the present invention enhances memory as an integral part of learning, as memory enables the storage and retrieval of information that was learned. In another embodiment, enhancing learning which includes memory is enhancing the capacity to record the outcome of a learning process. In another embodiment, enhancing learning is enhancing the ability to link new knowledge, by association. In another embodiment, enhancing learning is enhancing the framework of existing knowledge. In another embodiment, enhancing learning is enhancing memory in terms of reconstruction. In another embodiment, enhancing learning is enhancing spatial and/or non-spatial learning.

In another embodiment, learning is rule learning. In another embodiment, learning is set learning. In another embodiment, learning is spatial learning. In another embodiment, learning is location learning. In another embodiment, learning is conditioning learning and/or recording.

In another embodiment, learning is a result of habituation. In another embodiment, learning is a result of classical conditioning and/or operant conditioning (such as exemplified herein). In another embodiment, learning is a result of higher order forms learning, such rule learning (such as exemplified herein) and learning set (defined as a readiness or predisposition to learn developed from previous learning experiences, as when an organism learns to solve each successive problem of equal or increasing difficulty in fewer trials, seen in many animal species, or as a result of more complex activities such as play. In another embodiment, learning is not exclusively dependent on conscious awareness.

In another embodiment, learning comprises memory or memorization. In another embodiment, increase or enhancement in memory or memorization comprises changes in strength of connections between neurons in the relevant networks underling memory storage. In another embodiment, increase or enhancement in memory or memorization comprises modifications in intrinsic neuronal properties. In another embodiment, increase or enhancement in learning as described herein comprises behavioral changes.

In another embodiment, enhancing learning is enhancing sensory memory. In another embodiment, enhancing learning is enhancing short-term memory. In another embodiment, enhancing learning is enhancing long-term memory. In another embodiment, enhancing learning is enhancing memorization. In another embodiment, enhancing learning is enhancing declarative memory or explicit memory. In another embodiment, enhancing learning is enhancing implicit memory.

In another embodiment, enhancing learning is enhancing learning ability. In another embodiment, enhancing learning is enhancing mental capacity. In another embodiment, enhancing learning results in intelligence enhancement. In another embodiment, enhancing learning is attaining higher rates of learning without unacceptable reduction of comprehension or retention.

In another embodiment, enhancing learning is inducing or promoting active learning. In another embodiment, enhancing learning in a subject is inducing a cognitively active state. In another embodiment, enhancing learning is inducing or promoting reason (a mental faculty). In another embodiment, enhancing learning is promoting study skills.

In another embodiment, enhancing learning contributes to success in school. In another embodiment, enhancing learning in a subject results in better learning achievements such as grades.

In another embodiment, improving cognitive function (e.g., enhancing learning) is achieved by enhancement in intrinsic neuronal excitability which enhances higher-orders form of learning, such as rule learning and learning set. In another embodiment, a kainate receptor activator or a GluR6 receptor activator induces long term reduction of potassium currents that control the frequency of action potentials firing in hippocampal neurons, such that is induced by brief activation of kainate receptors or GluR6 receptors, serve as a general mechanism for enhanced learning. In another embodiment, enhancing learning by administering to a subject a kainate receptor activator or GluR6 receptor activator induces long-term changes in firing patterns of hippocampal neurons that in turn would not only enhance performance in the particular task for which the subject is trained, but has a broader affect on the hippocampal network.

In another embodiment, enhancing learning induces entry into a 'learning mode'. In another embodiment, enhancing learning includes the entry of the hippocampus into a 'learning mode'. In another embodiment, enhancing learning via a kainate receptor activator or a GluR6 receptor activator, increases learning capability in a range of hippocampus-dependent tasks. In another embodiment, activation of a kainate receptor or a GluR6 receptor according to the invention results in induction of neuronal excitability in hippocampus neurons. In another embodiment, activation of a kainate receptor or a GluR6 receptor according to the invention results in enhanced learning capability of a novel hippocampus-dependent task. In another embodiment, olfactory discrimination rule learning after activation of a kainate receptor or a GluR6 receptor, results not only in better olfactory discrimination tasks, but also in enhanced learning capability of a novel hippocampus-dependent task (the Morris water maze).

In another embodiment, activation of a kainate receptor or a GluR6 receptor according to the invention results in enhancement of neuronal excitability in the piriform (olfactory) cortex, in the hippocampus and the amygdale.

The Subject

In another embodiment, a subject in need of a treatment according to a method such as described herein is afflicted with a cognitive and/or degenerative brain disorder. In another embodiment, a subject in need of a treatment according to a method such as described herein is suffering from memory loss. In another embodiment, a subject in need of a treatment according to a method such as described herein is suffering from a progressive loss of memory, cognition, reasoning, judgment, emotional stability, or any combination thereof.

In another embodiment, a subject in need of a treatment according to a method such as described herein is suffering from Alzheimer's disease (AD). In another embodiment, a subject in need of a treatment according to a method such as described herein is suffering from dementia. In another embodiment, a subject in need of a treatment according to a method such as described herein is suffering from age associated memory impairment. In another embodiment, a subject in need of a treatment according to a method such as described herein is suffering from a learning deficit.

In another embodiment, a subject in need of a treatment according to a method such as described herein is suffering from multi-infarct dementia. In another embodiment, a subject in need of a treatment according to a method such as described herein is suffering from mixed organic brain syndrome metabolic encephalopathies of various origins. In another embodiment, a subject in need of a treatment according to a method such as described herein is suffering from alcoholic dementia. In another embodiment, a subject in need of a treatment according to a method such as described herein is suffering from a learning disorder. In another embodiment, a subject in need of a treatment according to a method such as described herein is suffering from loss of learning and memory associated with neuronal damage.

In another embodiment, a subject in need of a treatment according to a method such as described herein is suffering from a learning disability caused by a non-degenerative disorder. In another embodiment, a subject in need of a treatment according to a method such as described herein is suffering from a cognitive impairment. In another embodiment, a subject in need of a treatment according to a method such as described herein is suffering from an age-related cognitive decline. In another embodiment, a subject in need of a treatment according to a method such as described herein is suffering from a cerebral senility. In another embodiment, a subject in need of a treatment according to a method such as described herein is suffering from vascular dementia. In another embodiment, a subject in need of a treatment according to a method such as described herein is suffering from AIDS-associated dementia. In another embodiment, a subject in need of a treatment according to a method such as described herein is suffering from electric shock induced amnesia. In another embodiment, a subject in need of a treatment according to a method such as described herein is suffering from Parkinson's disease. In another embodiment, a subject in need of a treatment according to a method such as described herein is suffering from Down's syndrome. In another embodiment, a subject in need of a treatment according to a method such as described herein is suffering from stroke. In another embodiment, a subject in need of a treatment according to a method such as described herein is suffering from traumatic brain injury. In another embodiment, a subject in need of a treatment according to a method such as described herein is suffering from Huntington's disease. In another embodiment, a subject in need of a treatment according to a method such as described herein is suffering from an attention deficit disorder.

In another embodiment, a subject in need of a treatment according to a method such as described herein is a subject that needs to improve memory and learning ability. In another embodiment, a subject in need of a treatment according to a method such as described herein is a healthy subject that needs to improve memory and learning ability.

In another embodiment, the subject is a human subject. In another embodiment, the subject is a farm animal. In another embodiment, the subject is a dog. In another embodiment, the subject is a rescue animal. In another embodiment, the subject is an animal used by a rescue team. In another embodiment, the subject is an animal used by a police force. In another embodiment, the subject is a horse. In another embodiment, the subject is a monkey. In another embodiment, the subject is a pig.

Formulations/Dosage

In another embodiment, a kainate receptor activator or a GLuR6 receptor activator of the present invention is administered in a dose of 1-90 micrograms per ml. In another embodiment, a kainate receptor activator or a GLuR6 receptor activator of the present invention is administered in a dose of 1-50 micrograms per ml. In another embodiment, a kainate receptor activator or a GLuR6 receptor activator of the present invention is administered in a dose of 1-25 micrograms per ml. In another embodiment, a kainate receptor activator or a GLuR6 receptor activator of the present invention is administered in a dose of 50-90 micrograms per ml. In another embodiment, a kainate receptor activator or a GLuR6 receptor activator of the present invention is administered in a dose of 10-50 micrograms per ml.

Various embodiments of dosage ranges are contemplated by this invention. The dosage of the kainate receptor activator or the GLuR6 receptor activator of the present invention, in one embodiment, is in the range of 0.005-100 mg/day. In another embodiment, the dosage is in the range of 0.005-5 mg/day. In another embodiment, the dosage is in the range of 0.01-50 mg/day. In another embodiment, the dosage is in the range of 0.1-20 mg/day. In another embodiment, the dosage is in the range of 0.1-10 mg/day. In another embodiment, the dosage is in the range of 0.01-5 mg/day. In another embodiment, the dosage is in the range of 0.001-0.01 mg/day. In another embodiment, the dosage is in the range of 0.001-0.1 mg/day. In another embodiment, the dosage is in the range of 0.1-5 mg/day. In another embodiment, the dosage is in the range of 0.5-50 mg/day. In another embodiment, the dosage is in the range of 0.2-15 mg/day. In another embodiment, the dosage is in the range of 0.8-65 mg/day. In another embodiment, the dosage is in the range of 1-50 mg/day. In another embodiment, the dosage is in the range of 5-10 mg/day. In another embodiment, the dosage is in the range of 8-15 mg/day. In another embodiment, the dosage is in a range of 10-20 mg/day. In another embodiment, the dosage is in the range of 20-40 mg/day. In another embodiment, the dosage is in a range of 60-120 mg/day. In another embodiment, the dosage is in the range of 12-40 mg/day. In another embodiment, the dosage is in the range of 40-60 mg/day. In another embodiment, the dosage is in a range of 50-100 mg/day. In another embodiment, the dosage is in a range of 1-60 mg/day. In another embodiment, the dosage is in the range of 15-25 mg/day. In another embodiment, the dosage is in the range of 5-10 mg/day. In another embodiment, the dosage is in the range of 55-65 mg/day.

The dosage of the kainate receptor activator or the GLuR6 receptor activator of the present invention, in one embodiment, is in the range of 0.005-100 mg/Kg body weight. In another embodiment, the dosage is in the range of 0.005-5 mg/Kg body weight. In another embodiment, the dosage is in the range of 0.01-50 mg/Kg body weight. In another embodiment, the dosage is in the range of 0.1-20 mg/Kg body weight. In another embodiment, the dosage is in the range of 0.1-10 mg/Kg body weight. In another embodiment, the dosage is in the range of 0.01-5 mg/Kg body weight. In another embodiment, the dosage is in the range of 0.001-0.01 mg/Kg body weight. In another embodiment, the dosage is in the range of 0.001-0.1 mg/Kg body weight. In another embodiment, the dosage is in the range of 0.1-5 mg/Kg body weight. In another embodiment, the dosage is in the range of 0.5-50 mg/Kg body weight. In another embodiment, the dosage is in the range of 0.2-15 mg/Kg body weight. In another embodiment, the dosage is in the range of 0.8-65 mg/Kg body weight. In another embodiment, the dosage is in the range of 1-50 mg/Kg body weight. In another embodiment, the dosage is in the range of 5-10 mg/Kg body weight. In another embodiment, the dosage is in the range of 8-15 mg/Kg body weight. In another embodiment, the dosage is in a range of 10-20 mg/Kg body weight. In another embodiment, the dosage is in the range of 20-40 mg/Kg body weight. In another embodiment, the dosage is in a range of 60-120 mg/Kg body weight. In another embodiment, the dosage is in the range of 12-40 mg/Kg body weight. In another embodiment, the dosage is in the range of 40-60 mg/Kg body weight. In another embodiment, the dosage is in a range of 50-100 mg/Kg body weight. In another embodiment, the dosage is in a range of 1-60 mg/Kg body weight. In another embodiment, the dosage is in the range of 15-25 mg/Kg body weight.

In another embodiment, a kainate receptor activator or a GLuR6 receptor activator is formulated in an intranasal dosage form. In another embodiment, a kainate receptor activator or a GLuR6 receptor activator is formulated in an injectable dosage form. In another embodiment, a kainate receptor activator or a GLuR6 receptor activator is administered to a subject in a dose ranging from 0.0001 mg to 0.6 mg.

In another embodiment, a kainate receptor activator or a GLuR6 receptor activator is administered to a subject in a dose ranging from 1-100 micrograms. In another embodiment, a kainate receptor activator or a GLuR6 receptor activator is administered to a subject in a dose ranging from 10-80 micrograms. In another embodiment, a kainate receptor activator or a GLuR6 receptor activator is administered to a subject in a dose ranging from 20-60 micrograms. In another embodiment, a kainate receptor activator or a GLuR6 receptor activator is administered to a subject in a dose ranging from 10-50 micrograms. In another embodiment, a kainate receptor activator or a GLuR6 receptor activator is administered to a subject in a dose ranging from 40-80 micrograms. In another embodiment, a kainate receptor activator or a GLuR6 receptor activator is administered to a subject in a dose ranging from 10-30 micrograms. In another embodiment, a kainate receptor activator or a GLuR6 receptor activator is administered to a subject in a dose ranging from 30-60 micrograms.

In another embodiment, a kainate receptor activator or a GLuR6 receptor activator is administered to a subject in a dose ranging from 0.2 mg to 2 mg. In another embodiment a kainate receptor activator or a GLuR6 receptor activator is administered to a subject in a dose ranging from 2 mg to 6 mg. In another embodiment, a kainate receptor activator or a GLuR6 receptor activator is administered to a subject in a dose ranging from 4 mg to 10 mg. In another embodiment, a GLuR6 receptor activator is administered to a subject in a dose ranging from 5 mg and 15 mg.

In another embodiment, the dosage is in a range of 50-500 mg/day. In another embodiment, the dosage is in a range of 50-150 mg/day. In another embodiment, the dosage is in a range of 100-200 mg/day. In another embodiment, the dosage is in a range of 150-250 mg/day. In another embodiment, the dosage is in a range of 200-300 mg/day. In another embodiment, the dosage is in a range of 250-400 mg/day. In another embodiment, the dosage is in a range of 300-500 mg/day. In another embodiment, the dosage is in a range of 350-500 mg/day.

In one embodiment, the dosage is 20 mg/day. In one embodiment, the dosage is 30 mg/day. In one embodiment, the dosage is 40 mg/day. In one embodiment, the dosage is 50 mg/day. In one embodiment, the dosage is 0.01 mg/day. In another embodiment, the dosage is 0.1 mg/day. In another embodiment, the dosage is 1 mg/day. In another embodiment, the dosage is 0.530 mg/day. In another embodiment, the dosage is 0.05 mg/day. In another embodiment, the dosage is 50 mg/day. In another embodiment, the dosage is 10 mg/day. In another embodiment, the dosage is 20-70 mg/day. In another embodiment, the dosage is 5 mg/day.

In another embodiment, the dosage is 1-90 mg/day. In another embodiment, the dosage is 1-90 mg/2 days. In another embodiment, the dosage is 1-90 mg/3 days. In another embodiment, the dosage is 1-90 mg/4 days. In another embodiment, the dosage is 1-90 mg/5 days. In another embodiment, the dosage is 1-90 mg/6 days. In another embodiment, the dosage is 1-90 mg/week. In another embodiment, the dosage is 1-90 mg/9 days. In another embodiment, the dosage is 1-90 mg/11 days. In another embodiment, the dosage is 1-90 mg/14 days.

In another embodiment, a kainate receptor activator or a GLuR6 receptor activator dosage is 10-50 mg/day. In another embodiment, the dosage is 10-50 mg/2 days. In another embodiment, the dosage is 10-50 mg/3 days. In another embodiment, the dosage is 10-50 mg/4 days. In another embodiment, the dosage is 10-50 micrograms mg/5 days. In another embodiment, the dosage is 10-50 mg/6 days. In another embodiment, the dosage is 10-50 mg/week. In another embodiment, the dosage is 10-50 mg/9 days. In another embodiment, the dosage is 10-50 mg/11 days. In another embodiment, the dosage is 10-50 mg/14 days.

In one embodiment, determination of a therapeutically effective amount is well within the capability of those skilled in the art.

In another embodiment, a kainate receptor activator or a GLuR6 receptor activator of the present invention is administered by intramuscular (IM) injection, subcutaneous (SC) injection, or intravenous (IV) injection once a week. In another embodiment, a kainate receptor activator or a GLuR6 receptor activator of the present invention is administered by intramuscular (IM) injection, subcutaneous (SC) injection, or intravenous (IV) injection once a day. In another embodiment, a kainate receptor activator or a GLuR6 receptor activator of the present invention is administered by intramuscular (IM) injection, subcutaneous (SC) injection, or intravenous (IV) injection twice a week. In another embodiment, a kainate receptor activator or a GLuR6 receptor activator of the present invention is administered by intramuscular (IM) injection, subcutaneous (SC) injection, or intravenous (IV) injection twice a day.

In another embodiment, a kainate receptor activator or a GLuR6 receptor activator of the present invention can be provided to the individual per se. In one embodiment, a kainate receptor activator or a GLuR6 receptor activator of the present invention can be provided to the individual as part of a pharmaceutical composition where it is mixed with a pharmaceutically acceptable carrier.

In another embodiment, a "pharmaceutical composition" refers to a preparation of one or more of the active ingredients described herein with other chemical components such as physiologically suitable carriers and excipients. The purpose of a pharmaceutical composition is to facilitate administration of a compound to an organism.

In another embodiment, "active ingredient" refers to the kainate receptor activator or a GLuR6 receptor activator, which is accountable for the biological effect.

In one embodiment, the present invention provides combined preparations. In one embodiment, "a combined preparation" defines especially a "kit of parts" in the sense that the combination partners as defined above can be dosed independently or by use of different fixed combinations with distinguished amounts of the combination partners i.e., simultaneously, concurrently, separately or sequentially. In some embodiments, the parts of the kit of parts can then, e.g., be administered simultaneously or chronologically staggered, that is at different time points and with equal or different time intervals for any part of the kit of parts. The ratio of the total amounts of the combination partners, in some embodiments, can be administered in the combined preparation. In one embodiment, the combined preparation can be varied, e.g., in order to cope with the needs of a subject or patient subpopulation to be treated due to a particular disease, a particular condition, severity of disease or condition, age, sex, or body weight as can be readily made by a person skilled in the art.

In another embodiment, the phrases "physiologically acceptable carrier" and "pharmaceutically acceptable carrier" which be interchangeably used refer to a carrier or a diluent that does not cause significant irritation to an organism and does not abrogate the biological activity and properties of the administered compound. An adjuvant is included under these phrases. In one embodiment, one of the ingredients included in the pharmaceutically acceptable carrier can be for example polyethylene glycol (PEG), a biocompatible polymer with a wide range of solubility in both organic and aqueous media (Mutter et al. (1979)).

In another embodiment, "excipient" refers to an inert substance added to a pharmaceutical composition to further facilitate administration of an active ingredient. In one embodiment, excipients include calcium carbonate, calcium phosphate, various sugars and types of starch, cellulose derivatives, gelatin, vegetable oils and polyethylene glycols.

Techniques for formulation and administration of drugs are found in "Remington's Pharmaceutical Sciences," Mack Publishing Co., Easton, Pa., latest edition, which is incorporated herein by reference.

In another embodiment, suitable routes of administration, for example, include oral, rectal, transmucosal, transnasal, intestinal or parenteral delivery, including intramuscular, subcutaneous and intramedullary injections as well as intrathecal, direct intraventricular, intravenous, intraperitoneal, intranasal, or intraocular injections.

In another embodiment, the preparation is administered in a local rather than systemic manner, for example, via injection of the preparation directly into a specific region of a patient's body such as the brain.

Oral administration, of a kainate receptor activator or a GLuR6 receptor activator, in one embodiment, comprises a unit dosage form comprising tablets, capsules, lozenges, chewable tablets, suspensions, emulsions and the like. Such unit dosage forms comprise a safe and effective amount of a kainate receptor activator or a GLuR6 receptor activator.

The pharmaceutically-acceptable carriers suitable for the preparation of unit dosage forms for peroral administration are well-known in the art. In some embodiments, tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. In one embodiment, glidants such as silicon dioxide can be used to improve flow characteristics of the powder-mixture. In one embodiment, coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. In some embodiments, the selection of carrier components depends on secondary considerations like taste, cost, and shelf stability, which are not critical for the purposes of this invention, and can be readily made by a person skilled in the art.

In one embodiment, the oral dosage form comprises predefined release profile. In one embodiment, the oral dosage form of the present invention comprises an extended release tablets, capsules, lozenges or chewable tablets. In one embodiment, the oral dosage form of the present invention comprises a slow release tablets, capsules, lozenges or chewable tablets. In one embodiment, the oral dosage form of the present invention comprises an immediate release tablets, capsules, lozenges or chewable tablets. In one embodiment, the oral dosage form is formulated according to the desired release profile of the pharmaceutical active ingredient as known to one skilled in the art.

Peroral compositions, in some embodiments, comprise liquid solutions, emulsions, suspensions, and the like. In some embodiments, pharmaceutically-acceptable carriers suitable for preparation of such compositions are well known in the art. In some embodiments, liquid oral compositions comprise from about 0.001% to about 0.933% of a kainate receptor activator or a GLuR6 receptor activator, or in another embodiment, from about 0.01% to about 10%.

In some embodiments, compositions for use in the methods of this invention comprise solutions or emulsions, which in some embodiments are aqueous solutions or emulsions comprising a safe and effective amount of a kainate receptor activator or a GLuR6 receptor activator of the present invention and optionally, other compounds, intended for topical intranasal administration. In some embodiments, a kainate receptor activator or GLuR6 receptor activator compositions comprise from about 0.001% to about 10.0% w/v of a subject compound, more preferably from about 00.1% to about 2.0, which is used for systemic delivery of the compounds by the intranasal route.

In another embodiment, the pharmaceutical compositions are administered by intravenous, intra-arterial, or intramuscular injection of a liquid preparation. In some embodiments, liquid formulations include solutions, suspensions, dispersions, emulsions, oils and the like. In one embodiment, the pharmaceutical compositions are administered intravenously, and are thus formulated in a form suitable for intravenous administration. In another embodiment, the pharmaceutical compositions are administered intra-arterially, and are thus formulated in a form suitable for intra-arterial administration. In another embodiment, the pharmaceutical compositions are administered intramuscularly, and are thus formulated in a form suitable for intramuscular administration.

Further, in another embodiment, the pharmaceutical compositions are administered topically to body surfaces, and are thus formulated in a form suitable for topical administration. Suitable topical formulations include gels, ointments, creams, lotions, drops and the like. For topical administration, the compounds of the present invention are combined with an additional appropriate therapeutic agent or agents, prepared and applied as solutions, suspensions, or emulsions in a physiologically acceptable diluent with or without a pharmaceutical carrier.

In one embodiment, pharmaceutical compositions of the present invention are manufactured by processes well known in the art, e.g., by means of conventional mixing, dissolving, granulating, dragee-making, levigating, emulsifying, encapsulating, entrapping or lyophilizing processes.

In one embodiment, a pharmaceutical composition for use in accordance with the present invention is formulated in conventional manner using one or more physiologically acceptable carriers comprising excipients and auxiliaries, which facilitate processing of the active ingredients into preparations which, can be used pharmaceutically. In one embodiment, formulation is dependent upon the route of administration chosen.

In one embodiment, injectables, of the invention are formulated in aqueous solutions. In one embodiment, injectables, of the invention are formulated in physiologically compatible buffers such as Hank's solution, Ringer's solution, or physiological salt buffer. In some embodiments, for transmucosal administration, penetrants appropriate to the barrier to be permeated are used in the formulation. Such penetrants are generally known in the art.

In one embodiment, the preparations described herein are formulated for parenteral administration, e.g., by bolus injection or continuous infusion. In some embodiments, formulations for injection are presented in unit dosage form, e.g., in ampoules or in multidose containers with optionally, an added preservative. In some embodiments, compositions are suspensions, solutions or emulsions in oily or aqueous vehicles, and contain formulatory agents such as suspending, stabilizing and/or dispersing agents.

The compositions also comprise, in some embodiments, preservatives, such as benzalkonium chloride and thimerosal and the like; chelating agents, such as edetate sodium and others; buffers such as phosphate, citrate and acetate; tonicity agents such as sodium chloride, potassium chloride, glycerin, mannitol and others; antioxidants such as ascorbic acid, acetylcystine, sodium metabisulfote and others; aromatic agents; viscosity adjustors, such as polymers, including cellulose and derivatives thereof; and polyvinyl alcohol and acid and bases to adjust the pH of these aqueous compositions as needed. The compositions also comprise, in some embodiments, local anesthetics or other actives. The compositions can be used as sprays, mists, drops, and the like.

In some embodiments, pharmaceutical compositions for parenteral administration include aqueous solutions of the active preparation in water-soluble form. Additionally, suspensions of the active ingredients, in some embodiments, are prepared as appropriate oily or water based injection suspensions. Suitable lipophilic solvents or vehicles include, in some embodiments, fatty oils such as sesame oil, or synthetic fatty acid esters such as ethyl oleate, triglycerides or liposomes. Aqueous injection suspensions contain, in some embodiments, substances, which increase the viscosity of the suspension, such as sodium carboxymethyl cellulose, sorbitol or dextran. In another embodiment, the suspension also contain suitable stabilizers or agents which increase the solubility of the active ingredients to allow for the preparation of highly concentrated solutions.

In another embodiment, the active compound can be delivered in a vesicle, in particular a liposome (see Langer, *Science* 249:1527-1533 (1990); Treat et al, in Liposomes in the Therapy of Infectious Disease and Cancer, Lopez-Berestein and Fidler (eds.), Liss, N.Y., pp. 353-365 (1989); Lopez-Berestein, ibid., pp. 317-327; see generally ibid).

In another embodiment, the pharmaceutical composition delivered in a controlled release system is formulated for intravenous infusion, implantable osmotic pump, transdermal patch, liposomes, or other modes of administration. In one embodiment, a pump is used (see Langer, supra; Sefton, CRC Crit. Ref. *Biomed. Eng.* 14:201 (1987); Buchwald et al, Surgery 88:507 (1980); Saudek et al., *N. Engl. J. Med.* 321:574 (1989). In another embodiment, polymeric materials can be used. In yet another embodiment, a controlled release system can be placed in proximity to the therapeutic target, i.e., the brain, thus requiring only a fraction of the systemic dose (see, e.g., Goodson, in *Medical Applications of Controlled Release*, supra, vol. 2, pp. 115-138 (1984). Other controlled release systems are discussed in the review by Langer (*Science* 249:1527-1533 (1990).

In some embodiments, the active ingredient is in powder form for constitution with a suitable vehicle, e.g., sterile, pyrogen-free water based solution, before use. Compositions are formulated, in some embodiments, for atomization and inhalation administration. In another embodiment, compositions are contained in a container with attached atomizing means.

In one embodiment, the preparation of the present invention is formulated in rectal compositions such as suppositories or retention enemas, using, e.g., conventional suppository bases such as cocoa butter or other glycerides.

In some embodiments, pharmaceutical compositions suitable for use in context of the present invention include compositions wherein the active ingredients are contained in an amount effective to achieve the intended purpose-improvement of cognitive function, treatment of cognitive dysfunction, and/or enhancement of learning ability.

Some additional examples of substances which can serve as pharmaceutically-acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the Tween™ brand emulsifiers; wetting agents, such sodium lauryl sulfate; coloring agents; flavoring agents; tableting agents, stabilizers; antioxidants; preservatives; pyrogen-free water; isotonic saline; and phosphate buffer solutions. The choice of a pharmaceutically-acceptable carrier to be used in conjunction with the compound is basically determined by the way the compound is to be administered. If the subject compound is to be injected, in one embodiment, the pharmaceutically-acceptable carrier is sterile, physiological saline, with a blood-compatible suspending agent, the pH of which has been adjusted to about 7.4.

In addition, the compositions further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCI., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents(e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants.

Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, cellulose (e.g. Avicel™, RC-591), tragacanth and sodium alginate; typical wetting agents include lecithin and polyethylene oxide sorbitan (e.g. polysorbate 80). Typical preservatives include methyl paraben and sodium benzoate. In another embodiment, peroral liquid compositions also contain one or more components such as sweeteners, flavoring agents and colorants disclosed above.

The compositions also may include incorporation of the active material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance.

Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

In some embodiments, compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. In another embodiment, the modified compounds exhibit substantially longer half-lives in blood following intravenous injection than do the corresponding unmodified compounds. In one embodiment, modifications also increase the compound's solubility in aqueous solution, eliminate aggregation, enhance the physical and chemical stability of the compound, and greatly reduce the immunogenicity and reactivity of the compound. In another embodiment, the desired in vivo biological activity is achieved by the administration of such polymer-compound abducts less frequently or in lower doses than with the unmodified compound.

In some embodiments, preparation of effective amount or dose can be estimated initially from in vitro assays. In one embodiment, a dose can be formulated in animal models and such information can be used to more accurately determine useful doses in humans.

In one embodiment, toxicity and therapeutic efficacy of the active ingredients described herein can be determined by standard pharmaceutical procedures in vitro, in cell cultures or experimental animals. In one embodiment, the data obtained from these in vitro and cell culture assays and animal studies can be used in formulating a range of dosage for use in human. In one embodiment, the dosages vary depending upon the dosage form employed and the route of administration utilized. In one embodiment, the exact formulation, route of administration and dosage can be chosen by the individual physician in view of the patient's condition. [See e.g., Fingl, et al, (1975) "The Pharmacological Basis of Therapeutics", Ch. 1 p. 1].

In one embodiment, depending on the severity and responsiveness of the condition to be treated, dosing can be of a single or a plurality of administrations, with course of treatment lasting from several days to several weeks or until cure is effected or diminution of the disease state is achieved.

In one embodiment, the amount of a composition to be administered will, of course, be dependent on the subject being treated, the severity of the affliction, the manner of administration, the judgment of the prescribing physician, etc.

In one embodiment, compositions including the preparation of the present invention formulated in a compatible pharmaceutical carrier are also be prepared, placed in an appropriate container, and labeled for treatment of an indicated condition.

In another embodiment, the pharmaceutical composition comprises a kainate receptor activator or a GLuR6 receptor activator as described herein and complex carriers such as human serum albumin, polyols, sugars, and anionic surface active stabilizing agents. See, for example, WO 89/10756 (Hara et al.—containing polyol and p-hydroxybenzoate). In another embodiment, the pharmaceutical composition comprises a GLuR6 receptor activator as described herein and lactobionic acid and an acetate/glycine buffer. In another embodiment, the pharmaceutical composition comprises a GLuR6 receptor activator as described herein and amino acids, such as arginine or glutamate that increase the solubility of the kainate receptor activator or the GLuR6 receptor activator compositions in water. In another embodiment, the pharmaceutical composition comprises a lyophilized GLuR6 receptor activator as described herein and glycine or human serum albumin (HSA), a buffer (e g. acetate) and an isotonic agent (e.g NaCl). In another embodiment, the pharmaceutical composition comprises a lyophilized kainate receptor activator or GLuR6 receptor activator and phosphate buffer, glycine and HSA.

In another embodiment, the pharmaceutical composition comprising a kainate receptor activator or a GLuR6 receptor activator as described herein is stabilized when placed in buffered solutions having a pH between about 4 and 7.2. In another embodiment, the pharmaceutical composition comprising a kainate receptor activator or a GLuR6 receptor activator as described herein is stabilized with an amino acid as a stabilizing agent and in some cases a salt (if the amino acid does not contain a charged side chain).

In another embodiment, the pharmaceutical composition comprising a GLuR6 receptor activator provides a liquid formulation permitting storage for a long period of time in a liquid state facilitating storage and shipping prior to administration.

In another embodiment, the pharmaceutical composition comprising a GLuR6 receptor activator comprises polymeric microparticles. In another embodiment, the injectable pharmaceutical composition comprising a kainate receptor activator or a GLuR6 receptor activator comprises polymeric microparticles. In another embodiment, the pharmaceutical composition comprising a kainate receptor activator or a GLuR6 receptor activator, further comprises nanoparticles.

In one embodiment, compositions of the present invention are presented in a pack or dispenser device, such as an FDA approved kit, which contain one or more unit dosage forms containing the active ingredient. In one embodiment, the pack, for example, comprise metal or plastic foil, such as a blister pack. In one embodiment, the pack or dispenser device is accompanied by instructions for administration. In one embodiment, the pack or dispenser is accommodated by a notice associated with the container in a form prescribed by a governmental agency regulating the manufacture, use or sale of pharmaceuticals, which notice is reflective of approval by the agency of the form of the compositions or human or veterinary administration. Such notice, in one embodiment, is labeling approved by the U.S. Food and Drug Administration for prescription drugs or of an approved product insert.

In one embodiment, it will be appreciated that a kainate receptor activator or a GLuR6 receptor activator of the present invention can be provided to the individual with additional active agents to achieve an improved therapeutic effect as compared to treatment with each agent by itself. In another embodiment, measures (e.g., dosing and selection of the complementary agent) are taken to adverse side effects which are associated with combination therapies.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Materials and Methods
Behavioral Studies

Four hippocampus-dependent training paradigms were used: olfactory discrimination learning, Morris water maze, classical conditioning of the eyeblink response and fear conditioning. In addition, hippocampus-independent training paradigm, cue based learning in the water maze was used.

Olfactory Learning

Subjects were young adult male rats. Prior to training the rats were maintained on a 23.5 hours (hrs) water deprivation schedule with food available ad libitum.

Apparatus and Odors:

Olfactory discrimination protocol was performed in a 4-arm radial maze, with odors that are frequently used in the food industry (FIG. 1A). FIG. 1A is a schematic description of the 4-arm maze: an electronic 'start' command opens randomly two out of eight valves (V), releasing a positive-cue odor (P) into one of the arms and a negative-cue odor (N) into another. Eight seconds later, the two corresponding guillotine doors (D) are lifted to allow the rat to enter the selected arms. Upon reaching the far end of an arm (90 cm long), the rat body interrupts an infrared beam (I, arrow) and a drop of drinking water is released from a water hose (W) into a small drinking well (for a trained rat—only if the arm contains the positive-cue odor, for pseudo-trained rat—randomly). A trial ends when the rat interrupts a beam, or in 10 seconds, if no beam was interrupted. A fan is operated for 15 seconds between trials, to remove odors.

Training:

Olfactory training included 20 trials per day. Learning is considered to be acquired upon demonstration of at least 80% positive-cue choices for the last 10 trials of the day. A pseudo-trained group of age-matched rats was exposed to the same protocol of training, but with random water rewarding. An age-matched naive group of rats was water-deprived, without exposure to training. A day following memorization of a pair of odors by the rats in the trained group, both trained and pseudo trained groups were trained with a new pair of odors. The rats demonstrated increased capability to discriminate between new odors once they reach good performance with the first pair of odors. Thus, two learning phases can be clearly distinguished: The first phase of rule learning that usually requires 7-8 days, in which rats develop a strategy for performing the odor-discrimination task, and the second phase of enhanced learning capability, in which rats can learn new odors within 1-2 training days (FIG. 1B). FIG. 1B is a graph showing the odor pair training progression. Trained rats demonstrated acquisition of rule learning. Seven consecutive days of training were required for this group to reach criterion for discriminating between the first pair of odors (80% correct choices). Other groups usually require the same period also. Discrimination between any new pair of odors, starting from the third pair and forth, could be reached within one day. Values represent mean±SE. n=11 rats.

Protocols for trained and pseudo-trained rats were similar: an electronic 'start' command opens randomly two out of eight valves (V), releasing a positive-cue odor (P) into one of the arms and a negative-cue odor (N) into another. Eight seconds later, the two corresponding guillotine doors (D) are lifted to allow the rat to enter the selected arms. Upon reaching the far end of an arm (90 cm long), the rat body interrupts an infrared beam (I, arrow) and a drop of drinking water is released from a water hose (W) into a small drinking well (for trained rats: only if the arm contains the positive-cue odor; for pseudo-trained rats: randomly). A trial ends when the rat interrupts a beam, or within 10 seconds, if no beam is interrupted. A fan is operated for 15 seconds between trials, to remove residual odors.

Water Maze Training

Rats were trained in a circular pool, 1.8 m in diameter and 0.6 m high, containing water at 26±1° C. The pool occupied the center of a room and contained various salient cues. A 10-cm square transparent platform was hidden in a constant position in the pool with its surface submerged 1 cm below the water level. The rats were given four consecutive training sessions per day, starting from random locations around the pool each time. Each session lasted up to 120 sec. The measures used included the latency time (in seconds) to reach the platform.

Physiological Studies

Slice Preparation and Recordings:

brain slices of the pirofm cortex hippocampus are prepared and recordings were obtained from pyramidal neurons, with sharp electrodes for current clamp studies of AHP and neuronal adaptation. Data was collected from at least 20 neurons taken for 6 rats or more in each experimental group.

AHP and Neuronal Adaptation Measurements:

for after-hyper-polarization (AHP) measurement, neurons were depolarized in current clamp mode to $V_m$ of −60 mV with DC current injection, and 100 ms long depolarizing current steps were applied with intensity sufficient to evoke trains of 6 action potentials. AHP amplitude was measured from baseline to the peak of the hyperpolarizing voltage deflection that follows the spike train (FIGS. $2A_1$ and $2A_2$). The AHP value was determined from the averaged amplitude in 4-5 consecutive traces, evoked at intervals of 10 sec. FIGS. 2A1 and 2A2 show the same trace on different time scales. Neurons were held at membrane potential of −60 mV and post-burst AHP was generated by 100 ms depolarizing current step injection via the recording electrode, with intensity sufficient to generate a train of 6 action potentials.

For neuronal adaptation measurements, prolonged (1 sec) depolarizing current steps are applied to the neurons via the recording electrode at $V_{rest}$, with stimulus intensity of twice $I_{Threshold}$ (FIG. 2B). The firing frequency was measured between each of two spikes in the train, and values were normalized to the initial frequency at which the first two spikes are generated. FIG. 2B is a graph depicting an example for neuronal firing adaptation in layer II pyramidal cell. In response to a 1 sec depolarizing current step at current clamp mode, with stimulus intensity of Ithx2, the cell fired a train of action potentials with spiking frequency that is highest at the onset of the pulse and decreases considerably thereafter.

Example 1

Post Burst AHP Reduction Occurs when Rats Learn a Complex Rule

Figure 3B:
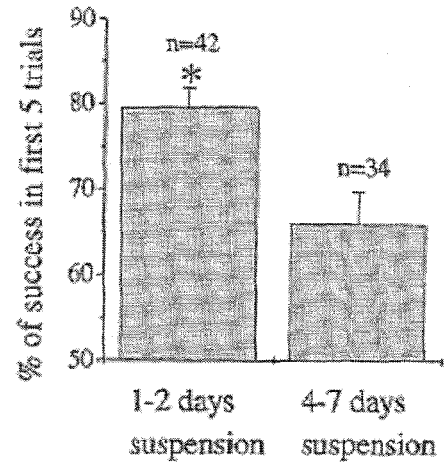

To examine whether AHP reduction in the piriform cortex is related to acquisition of 'rule learning' with odor discriminations, rats were trained with only one or two pairs of odors, until enhancement of learning rate was achieved. Thereafter, brain slices were prepared at various intervals (after the last training session). One to 3 days after training, AHPs following trains of six action potentials in neurons from 'mildly trained' rats were significantly smaller ($P \leq 0.05$) (6.7 6 2.0 mV, n 5 28) than in cells from the 'control' (8.3 6 1.6 mV, n 5 23) and 'naive' (8.2 6 2.7 mV, n 5 11) animals. The phenomenon was transient. Five days or more after the last training session, the average amplitude of the AHPs did not differ between neurons from 'trained' and 'control' (FIG. 3A). One and 3 days after the last training session the AHP amplitudes in neurons from 'trained' rats were significantly smaller than in 'controls' ($P \leq 0.05$). Five days or more after the last training session, AHP amplitudes were not significantly different between groups. Neurons were recorded from six 'trained' and six 'control' rats ("n" indicates the number of cells). Training suspension results in reduced learning capability In order to test whether training suspension is accompanied by reduced learning capability, the performance of rats when training with novel odors was examined after various suspension times. It was found that rats for which training was suspended for 4 days or more performed significantly ($P \leq 0.05$) worse than rats whose training was suspended for 1-2 days only (FIG. 3B). The performance of trained rats on the first five trials in a session declined, if training was suspended for 4 days or more ("n" represents the number of sessions, all performed in six rats).

Figure 3C:
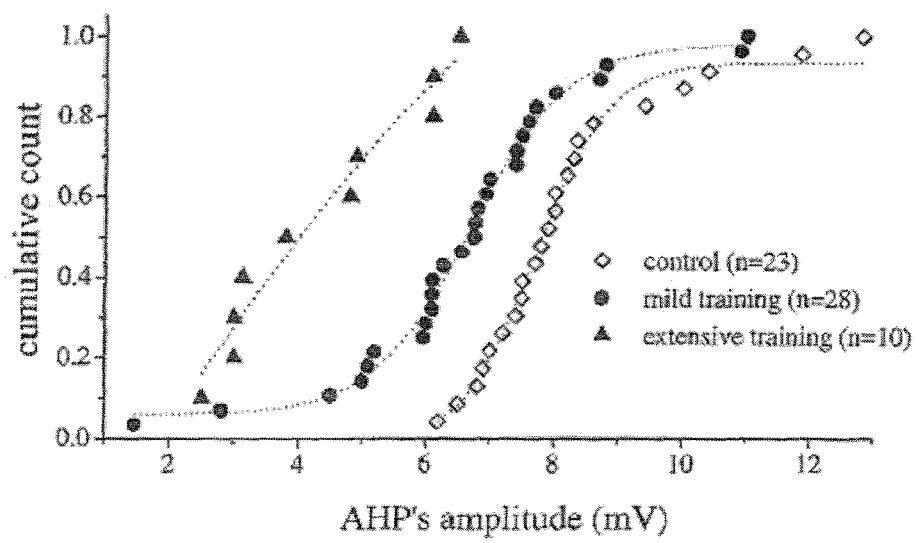
FIG. 3C is a graph depicting cumulative frequency distribution of AHP amplitudes in randomly sampled cells.

After-hyperpolarization reduction is observed in most sampled pyramidal neurons. If AHP reduction in the piriform cortex is related to a general enhancement of odor-learning capability, it was expected that AHP reduction would occur in a significant portion of the pyramidal cell population. Indeed, most of the neurons sampled from the rats trained with rule learning, and all the neurons sampled from the 'extensively trained' (trained with many odors) rats had smaller AHPs than the average AHP that was sampled in 'controls'. A cumulative frequency distribution of AHPs amplitudes in response to firing six action potentials is shown in FIG. 3C. With each point representing one cell, it is noticeable that the reduction of the averaged AHP amplitude is a result of the reduction in AHP in most of the sampled neurons of the rule learning trained group until and all neurons derived from the 'extensively trained' group. Hence, AHP reduction is widely distributed throughout the neuronal population after training, rather than being restricted to a small portion of the cells.

Example 2

Figure 4A:
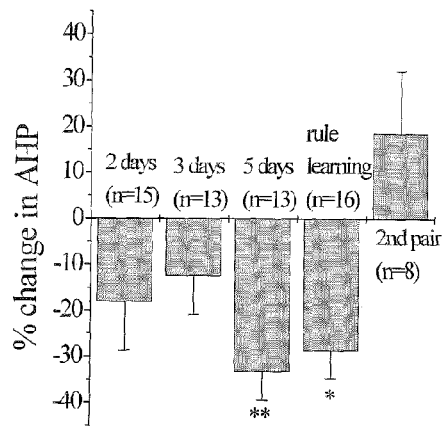
FIGS. 4A-4B are directed to olfactory-learning induced AHP reduction in CA1 neurons.
Figure 4B:
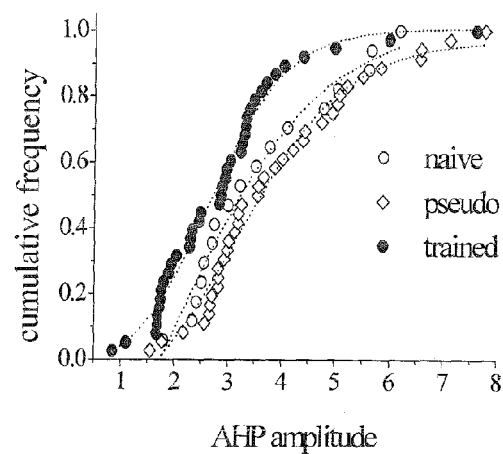

Olfactory Discrimination Learning Enhanced Neuronal Excitability in all Recorded Hippocampal Neurons As shown in FIG. 4A Post-burst AHP is reduced starting form the fifth day of training (e.g. before rule acquisition) until after training completion for the first pair of odors. Cumulative frequency histograms for AHP amplitude in neurons from trained, pseudo trained and naive rats were recorded. In FIG. 4B each point represents AHP amplitude in one cell. AHP amplitudes in neurons from trained rats create a curve that is smoothly shifted to the left along the X-axis, indicating that learning and reduction in AHP occur side by side throughout the neuronal population.

Figure 5A:
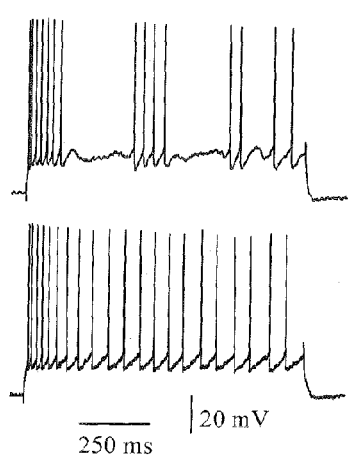
FIGS. 5A-5B are directed to enhanced neuronal excitability in CA1 neurons during olfactory learning.
Figure 5B:
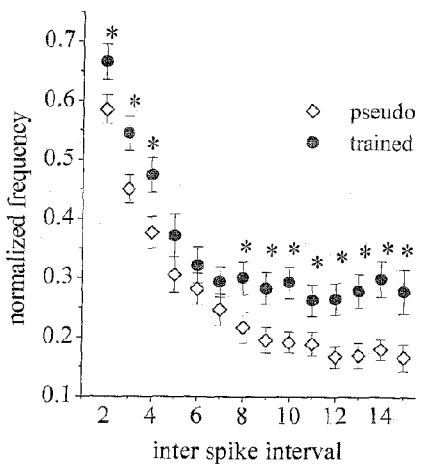

As shown in FIGS. 5A-B, repetitive action potentials firing are observed in neurons from a pseudo trained (5A, top panel) and a trained (5B, lower panel) rats in response to 1 sec pulse with stimulus intensity of Ithx2 enhanced neuronal excitability in CA1 neurons during olfactory learning. Frequency at each inter-stimulus interval (ISI) along the train was normalized to the initial frequency at the train onset. Starting from the 2nd interval, the averaged normalized frequency at most ISIs was significantly higher in neurons from trained rats (* $p<0.05$), compared to neurons from pseudo trained rats (n=25 cells in each group)

Thus OD learning is accompanied by reduced post-burst AHP and enhanced neuronal excitability in piriform cortex pyramidal neurons (FIGS. 2A-B and 3A-C). Moreover, these results demonstrate that similar modifications occur also in CA1 hippocampal neurons just prior to and during rule learning of the same task (FIGS. 4A-B and 5A-B). Importantly, it was unexpectedly found that kainate-induced post burst AHP reduction by activating kainate receptor-GluR6 receptors (FIGS. 7-9).

Example 3

Figure 6A:
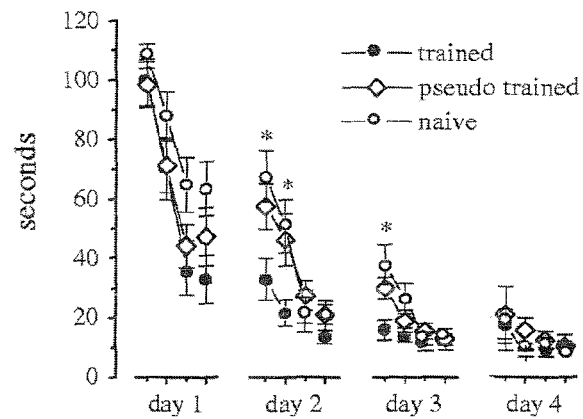
FIGS. 6A-B are directed to behavioral consequences of post-burst AHP reduction.
Figure 6B:
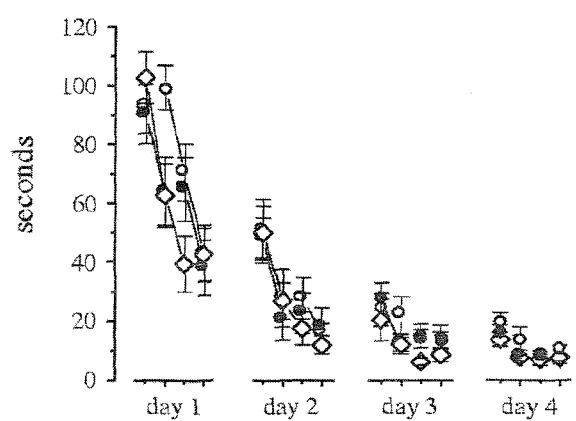

Acquisition of a Hippocampus-Dependent Task Enhances Acquisition of Other Hippocampus-Dependent Tasks Only while the Post Burst AHP is Reduced The results presented in FIGS. 6A-B clearly demonstrate that olfactory-trained rats perform better in the water maze than naive and olfactory pseudo trained rats. This phenomenon occurs only when excitability appears in hippocampal neurons as a result of learning-inducement. These data surprisingly demonstrate that learning-induced modifications in intrinsic membrane properties, such that induction by brief activation of the GluR6 receptor, results in an unexpected learning capability/ability enhancement.

As shown in FIG. 6A, olfactory discrimination (OD) learning in the olfactory maze enhances subsequent learning in the Morris water maze. Rats were exposed to the water maze on the same day that they acquired the rule (rule learning) in the olfactory maze. OD trained rats performed better then naive and pseudo-trained rats on the first two trials of day 2 and on the first trial of day 3 (*$P \leq 0.05$). Averaged values±SE are shown for 22 naïve rats, 21 trained rats and 19 pseudo-trained rats.

OD trained rats lost their advantage over control rats in water maze learning when the post-burst AHP resumes its control value (FIG. 6B). Training rats in the water maze after learning to discriminate between a second pair of odors (e.g. 3 days after rule learning, when the post-burst AHP resumes its initial value), resulted with performance similar to that of pseudo-trained and naive rats in the new task. Averaged values±SE are shown for 17 naive, 17 trained and 17 pseudo-trained rats.

Repetitive stimuli-induced long-lasting AHP reduction is occluded by learning. Twenty repetitive stimuli applied at 50 Hz significantly decreased the averaged AHP amplitude in neurons from naive rats (from 8.32 mV±2.1, n=31 to 6.85±2.5, n=14, p<0.05) and pseudo trained (from 7.98+2.2, n=21 to 6.33+2.7, n=14, p<0.05) rats (FIGS. 7A and C). Once induced, such decreased AHP remained stable for the total recording period. In sharp contrast, the post burst AHP in neurons from trained rats was not affected by the repetitive stimuli. The averaged AHP before (6.56±1.9, n=26) and after the repetitive stimuli (6.31±n=20) was similar (FIG.

7B,C). Consequently, the averaged values of the post burst AHP did not differ between the three groups.

Example 4

Kainate Receptors Mediate Long-Lasting Reductions of AHP

The experiments described herein demonstrate that long-term AHP reduction is induced via kainate receptors. Thus a target, a kainate receptor such as the GluR6 receptor, and a molecule activating the target, kainate, were unexpectedly identified. These discoveries enable the targeting of a GluR6 receptor via an activator such as kainate for inducing a learning mode in both normal individuals and individuals suffering from a learning deficiency. In other words, the results presented herein demonstrate that an elevation of learning capability can be achieved by the mere activation of a kainate receptor such as the GluR6 receptor for example by kainate and/or other activators described herein and/or known to one of skill in the art.

These experiments included a brief, ten minutes long, exposure to kainate. This exposure significantly decreased the averaged AHP amplitude in neurons from naive animals to 6.0±2.5 (n=16 (p<0.05)) and in neurons from pseudo trained rats to 6.63+2.4 (n=7 (p<0.05)). This decrease outlasted while kainate was present and was always apparent for the total length to kainate exposure (FIG. 8A).

The post burst AHP in neurons from trained rats was not affected by exposure to kainate. The averaged AHP in kainate induced, trained neurons was 6.63±2.4 (n=7). Thus, exposure to kainate did not affect the averaged values of the post burst AHP between the three groups (FIG. 8C).

The data presented in FIGS. 7A-C and 8A-C clearly demonstrates that learning-induced enhanced neuronal excitability is induced via short activation of kainate glutamatergic receptors. From reasons noted above, GluIR6 is the receptor mediating this long-term effect. The ability to single out a specific glutamatergic receptor, that its brief activation initiates a sequence of events leading to a general enhancement of learning capability, is of great significance for treating efficiently learning-deficits. Such a treatment is based on activation of the GluR6 receptor which induces a "learning mode" or enhances an inducible "learning mode" in a normal subject.

Example 5

GluR6 Knockout Mice are Incapable of Learning

To further demonstrate the intrinsic cross talk between GluR6 receptors and complex learning, GluR6 knockout mice were tested by a well accepted complex rule model.

As shown in FIGS. 9A and 9B the wild type animals have normal learning capabilities whereas GluR6 knockout animals are incapable of learning choices as clearly indicated by the results of the complex rule model test (FIG. 9A and reflected in FIG. 9B). Thus, it can be concluded that an operative GluR6 receptor is essential for learning. This experiment also demonstrates that the molecular learning pathway which involves GluR6 is pivotal throughout development and is not redundant.

Example 6

Kainate Application Enhances GluR6-Mediated Neuron Repetitive Spike Firing

Figure 10A:
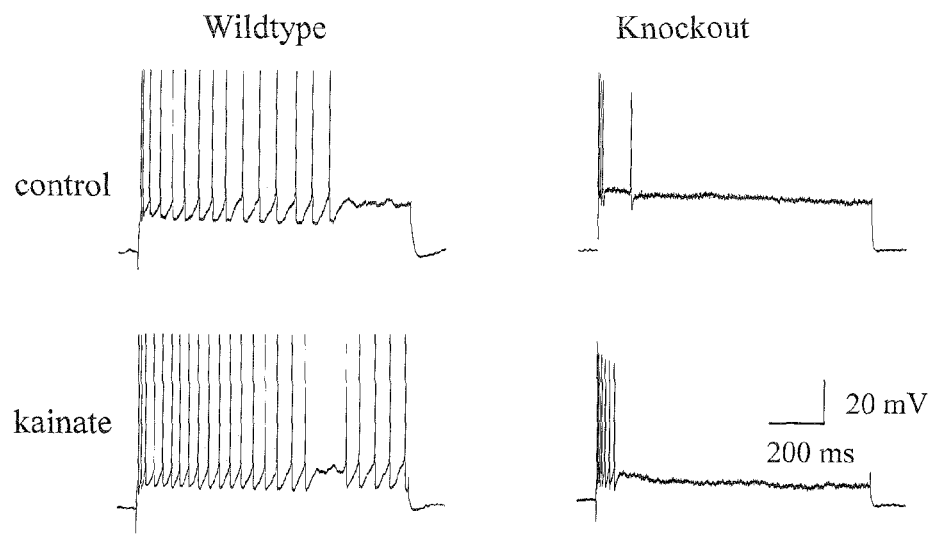
FIGS. 10A-B are directed to kainate application enhances repetitive spike firing in neurons of Wild Type (WT; GluR6+/+) mice as apposed to GluR6 knockout mice (GluR6−/−).
Figure 10B:
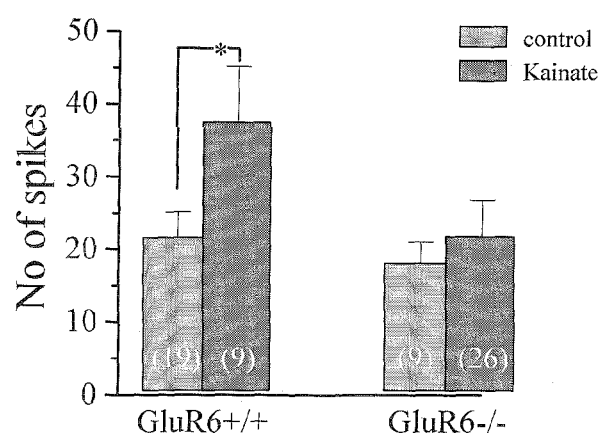

In response to a 1 sec depolarizing pulse with stimulus intensity of $I_{th}x2$, kainite application enhanced repetitive spike firing in neurons of Wild Type (WT; GluR6+/+) mice as apposed to GluR6 knockout mice (GluR6−/−) (FIG. 10A). FIG. 10B is a bar graph depicting the number of spikes following kainate application in GluR6+/+ and GluR6−/− neurons, as opposed to control, (n) depicts the number of neurons. Notably, while in wild types kainate application doubles the number of action potentials, it has no effect on neurons from GluR6 knockouts. While Example 5 demonstrated that operative GluR6 receptor is essential for learning, this Example indicates that kainate application enhances neuronal excitability such as by repetitive neurons spike firing.

Example 7

GluR6 Receptor Activation Reduced Enhances the Learning Ability

To further demonstrate the affect of GluR6 receptor activation on enhancement of the learning ability, homo-AMPA was applied to the brain ventricles of rats and the time required for complex olfactory learning was evaluated.

Homo-AMPA was dissolved in sterile saline with the addition of minimal amount of 0.1 M NaOH; then 0.1 M HCl was used to adjust pH (pH=7.2). 10 mg of Homo-AMPA dissolved in 200 microliters. The final volume was 250 microliter (Homo-AMPA in the saline+NaOH). A final amount of Homo-AMPA 500 nmol was injected into the brain ventricles of the tested rats. Learning evaluation was performed every day, 10 min after injections.

Figure 11A:
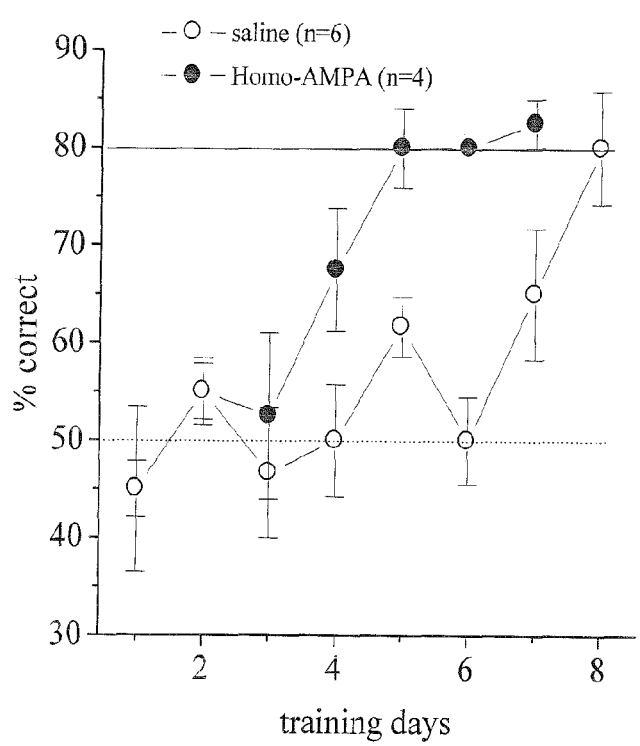
FIGS. 11A-B are directed to application of homo-AMPA ((RS)-2-amino-4-(3-hydroxy-5-methylisoxazol-4-yl)butyric acid) via the brain ventricles reduced the averaged time required for complex olfactory learning from eight days to less than five days, which is depicted in a line and bar graph (FIGS. 11A and 11B, respectively).
Figure 11B:
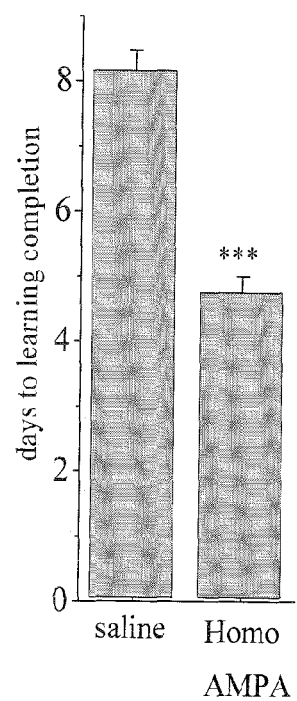

As seen in FIGS. 11A and 11B, the averaged number of training days required for learning completion was reduced from 8 days in saline injected rats (same rate as for untreated animals) to less than five days in homo-AMPA treated rats, with a highly significant difference (p<0.001).

The experiments provided herein demonstrate that AHP reduction, and its consequent enhancement in neuronal excitability, is the mechanism that enables neuronal ensembles to enter into a state which may be best termed "learning mode". This desired state lasts for up to several days and its behavioral manifestation includes enhanced learning capability in tasks that depend on these neuronal ensembles. Importantly, the activation of the glutamate receptor, GluR6, is pivotal to learning per-se and inducing its activity results in enhanced learning ability/capability.

Moreover, rule learning was accompanied by reduction of the post burst AHP while increase in the post burst AHP is accompanied by reduced learning capability. Such modifications occur throughout the neuronal cell population and explain the above processes.

Specifically, in the process of olfactory-discrimination learning, the post burst is reduced and neuronal excitability is transiently enhanced in hippocampal pyramidal neurons, while synaptic transmission remains at its control value. Induction of olfactory learning results in increased neuronal excitability in hippocampus, which in turn enhances the rats learning ability and capability as demonstrated in the Morris water maze (another hippocampus dependent task). Importantly, such general, unexpected, enhancement in learning ability/capability is present only for as long as the AHP is reduced, a process that is initiated exclusively by brief activation of the GluR6 receptors. Activation of the GluR6 receptors was accomplished by contacting these receptors with kainate. These evidences strongly suggest that enhanced excitability of hippocampal neurons serves as a mechanism for generalized enhancement of hippocampus-dependent learning capability.

In conclusion: it is impossible to reduce the post burst AHP in GluR6 knockout mice. These mice are also incapable of rule learning. Thus, complex learning requires a long term reduction in the AHP. Such long-term reduction can be obtained only by activating the kainate receptors and specifically the GluR6 receptors. Learning enhancement occurred as a result of inducing kainate receptors. Thus ligand, activators, and/or agonists of GluR6 receptors such as kainate are pivotal for treating disease-related and/or aging-related, learning-deficits, as well as enhancing a learning capability in healthy, normal learning, subjects.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A method of improving cognitive function of a human subject afflicted with a neurodegenerative disease in need thereof, comprising the step of administering to said subject a composition comprising an effective amount of an activator specific for the GluR6 kainate receptor wherein the activator specifically induces GluR6 receptor and not other glutamate receptors and significantly decreases the averaged after-hyperpolarization (AHP) amplitude in neurons of said subject, thereby improving the cognitive function of said subject, wherein improving cognitive function comprises enhancing a learning ability selected from the group consisting of conditioning learning, spatial learning and location learning, and wherein said activator is (2S,3S,4S)-3-(Carboxymethyl)-4-(prop-1-en-2-yl)pyrrolidine-2-carboxylic acid.

2. The method of claim 1, wherein said subject is additionally afflicted with an age-related cognitive impairment selected from the group consisting of Mild Cognitive Impairment (MCI), Age-Associated Memory Impairment (AAMI), and Age-related Cognitive Decline (ARCD).

3. The method of claim 2, wherein said subject is afflicted with MCI.

4. The method of claim 1, wherein said improving cognitive function further comprises enhancement of long term memory in said subject.

5. The method of claim 1, wherein said subject is afflicted with dementia.

6. The method of claim 1, wherein said subject is diagnosed with a low learning capability.

7. The method of claim 1, wherein the activator specific for the GluR6 is administered orally.

8. A method of improving cognitive function of a human subject afflicted with a neurodegenerative disease in need thereof, comprising the step of administering to said subject a composition comprising an effective amount of an activator specific for the GluR6 kainate receptor wherein the activator specifically activates GluR6 receptor and not other glutamate receptors, thereby improving the cognitive function of said subject wherein improving cognitive function comprises enhancing a learning ability selected from the group consisting of conditioning learning, spatial learning and location learning, and, wherein said activator is (2S,3S,4S)-3-(Carboxymethyl)-4-(prop-1-en-2-yl)pyrrolidine-2-carboxylic acid.

9. The method of claim 8, wherein said subject is additionally afflicted with an age-related cognitive impairment selected from the group consisting of Mild Cognitive Impairment (MCI), Age-Associated Memory Impairment (AAMI), and Age-related Cognitive Decline (ARCD).

10. The method of claim 9, wherein said subject is afflicted with MCI.

11. The method of claim 8, further comprising enhancing long term memory in said subject.

* * * * *